United States Patent [19]
Henry et al.

[11] Patent Number: 5,908,752
[45] Date of Patent: Jun. 1, 1999

[54] METHODS FOR PRODUCING PHOSPHOLIPID METABOLITES IN YEAST

[75] Inventors: Susan A. Henry; Jana L. Patton, both of Pittsburgh, Pa.; Peter Griac, Bratislava, Slovakia; Sepp D. Kohlwein, Graz, Austria

[73] Assignee: Carnegie Mellon University, Pittsburgh, Pa.

[21] Appl. No.: 08/852,450

[22] Filed: May 7, 1997

[51] Int. Cl.$^6$ ............................... C12Q 1/02; C12Q 1/68; C12N 1/18

[52] U.S. Cl. ................. 435/6; 435/29; 435/134; 435/155; 435/171; 435/194; 435/254.1; 435/254.11; 435/254.2; 435/254.21; 435/455

[58] Field of Search ................. 435/252.3, 254.1, 435/254.11, 254.2, 254.21, 172.1, 172.3, 155, 134, 199, 4, 29, 645, 455

[56] References Cited

PUBLICATIONS

Griac et al., J. Biol. Chem., vol. 271, No. 41, pp. 25692–25698, Oct. 11, 1996.
Cleves, A., et al., *Cell 64*: 789 (1991).
Bankaitis, V., et al., *Nature 347*: 561 (1990).
Novick, P., et al., *Cell 21*: 205 (1980).
Kennedy, E.P., et al., *J. Biol. Chem. 222*: 193 (1956).
Bremer, J., et al., *Biochem. Biophys. Acta. 37*: 173 (1960).
Griac, P., et al., *J. Biol. Chem. 271*: 25692 (1996).
McMaster, C.R., et al., *J. Bio. Chem. 269*: 14776 (1994).
McDonough, V.M., et al., *J. Bio. Chem. 270* (32): 18774 (1995).
McGee, T.P. et al, *J. Cell Biol. 124*: 273 (1994).
Summers, E.F., et al., *Genetics 120*: 909 (1988).
Cleves, A., et al., *Trends Cell Bio. 1*: 30 (1991b).
McGraw, P., et al, *Genetics 122*: 317 (1989).
Paltauf, F., et al., *The Molecular and Cellular Biology of Yeast Saccharomyces* (Broach, J., et al. eds.) vol. II, pp. 415–500, Cold Spring Harbor Laboratory Press, Plainview, NY (1992).
Bachhawat, N., et al, *J. Biol. Chem. 270*: 25087 (1995).
Klig, L.S., et al., *J. Bacteriol. 170*: 1878 (1988).
Shen, H., et al., *J. Biol. Chem. 271*: (1996).
Gietz, D., et al, *Nucl. Acids. Res. 20*: 1425 (1992).
Greenberg, M., et al., *Genetics 100*: 19 (1982).
Swede, M.J., et al., *Methods in Enzymology: Phospholipid Biosynthesis* (Vance, D.E., et al, eds.) vol. 29 pp. 21–34 (1992).
Lopes, J., et al, *Nucl. Acids. Res. 19*(7) 1687 (1991).
Hudak, K.A., et al., *Genetics 136*: 475 (1994).
Elion, E.A., et al., *Cell 39*: 663 (1984).
Hirsch, J.P., et al., *Mol. Cell. Biol. 6*(10): 3320 (1986).
Atkinson, K.D., et al., *J. Bacteriol. 141*: 558 (1980).
Steiner, M.R., et al., *Biochem. Biophys. Acta 260*: 222 (1972).
Kelley, M.J., et al, *J. Biol. Chem. 263*: 18078 (1988).
Becker, G.W., et al., *J. Bacteriol. 142*: 747 (1980).
Martin, T.W., *Biochem. Biophys. Acta 962*: 282 (1988).
Hosaka, K., et al., *J. Biol. Chem. 264*: 2053 (1989).
Angus, W.W., et al., *Arch. Biochem. Biophys. 151*: 483 (1972).
Lamping, E., et al., *Genetics 137*: 55 (1995).
Griac P., et al, Nato ASI Series: *Mol. Dynamics of Biological Membrane* (Op den Kamp, J.A.F. ed.) vol. H 96 pp. 339–346, Spinger–Vergag Berlin/Heidelberg (1996).
Jiranek. V., et al., *J. Bacteriol. 81*: 329 (1996).
Exton, J.H., *Biochem. Biophys. Acta 1212*: 26 (1994).
Lee, K.S., et al., *J. Biol. Chem. 269*: 19725 (1994).
Henry S.A., *Molecular Biology of the Yeast Saccharomyces: Metabolism & Gene Expression* (Strathern, J.N., et al. eds.) vol. 2, pp. 101–158, Cold Spring Harbor Lab, Cold Spring Harbor, NY (1982).
Greenberg, M.L., et al., *J. Bacteriol 153*: 791 (1983).
Letts, V.A., et al., *J. Bacteriol. 163*: 560 (1985).
Kodaki, T., et al., *J. Biol. Chem. 262*: 15428 (1987).
Carman, G.M., et al., *J. Biol. Chem. 271*: 13293 (1996).
Ktistakis, N.T., et al., *J. Cell Biol. 134*: 295 (1996).
Wirtz, K.W.A., et al., *Experientia 46*: 592 (1990).
Honigberg, S.M., et al., *Genetics 130*: 703 (1992).
Liscovitch, M., *J. Lipid Mediators Cell Signalling 14*: 215 (1996).
Greenberg, M.L., et al., *Microbiol. Rev. 60*: 1 (1996).
Rose, K., et al., *Proc. Natl. Acad. Sci. USA 92*: 1215 (1995).
Waksman, M., et al., *J. Biol. Chem. 271*: 2361 (1996).
Ella, K.M., et al., *Biochem. J. 314*: 15 (1996).

*Primary Examiner*—David Guzo
*Attorney, Agent, or Firm*—Reed Smith Shaw & McClay LLP

[57] ABSTRACT

Methods are provided for increased and controlled production of choline and inositol, choline and inositol metabolites, and choline- and inositol-containing phospholipids in yeast, comprising the step of increasing phosphatidylcholine (PC) turnover in yeast. Methods are also provided for detecting phospholipase D-mediated turnover of phosphatidylcholine in vivo in yeast, comprising an assay for choline excretion.

34 Claims, 12 Drawing Sheets

*cki1*

37°C

30°C

*sec14, cki1*

37°C

30°C wt

30°C

I −  I +

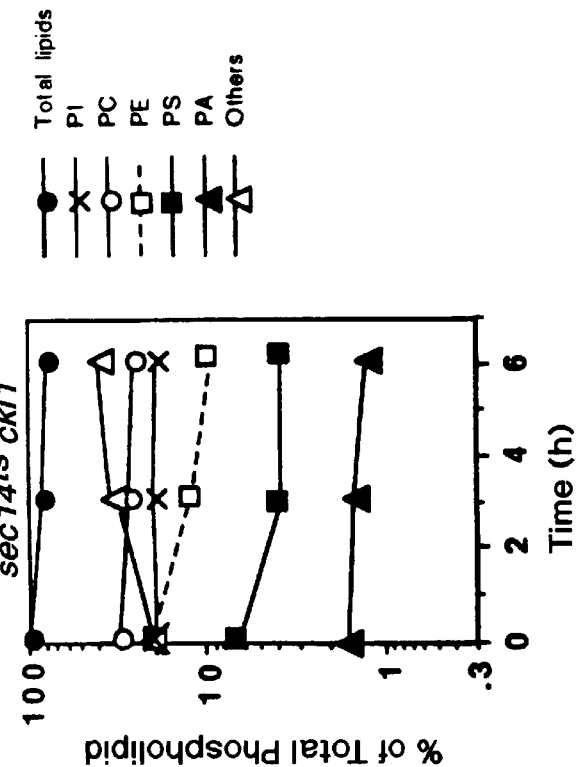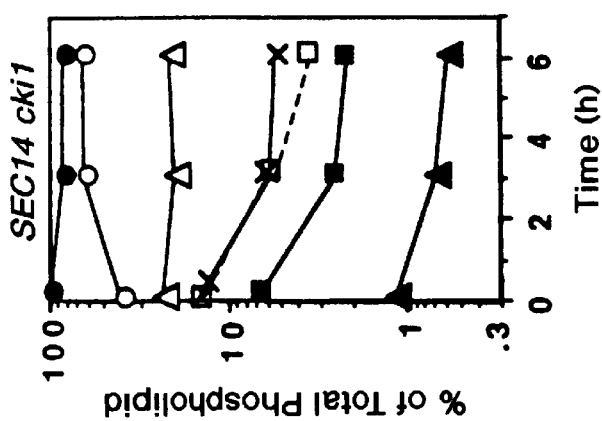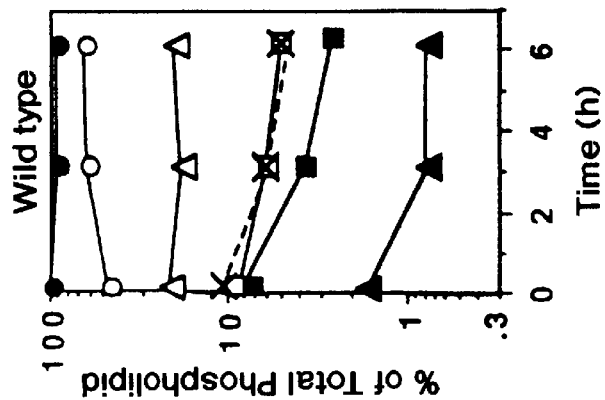
FIG. 6C
FIG. 6B
FIG. 6A

METHODS FOR PRODUCING PHOSPHOLIPID METABOLITES IN YEAST

ACKNOWLEDGMENT

The present invention was developed in part with government support under grant number GM-19629 awarded by the National Institutes of Health. The government has certain rights in this invention.

FIELD OF THE INVENTION

The present invention relates generally to methods for regulating the levels of phospholipids and phospholipid metabolites in yeast cells. The present invention also generally relates to methods for detecting turnover of phosphatidylcholine in vivo. The methods of the present invention allow for economical production of inositol and choline for human or animal consumption.

BACKGROUND

Phospholipid transfer proteins capable of exchanging phospholipids between membrane bilayers in vitro have been extensively characterized, but the role of these proteins in vivo has been more difficult to establish. See, for example, Cleves, A., et al., *Cell* 64:789 (1991), the disclosure of which is incorporated herein by reference. (Hereafter all additional citations of a particular publication shall be to the author(s) and year only.) A breakthrough occurred with the discovery that the SEC14 gene of *Saccharomyces cerevisiae* encodes the phosphatidylinositol (PI)/phosphatidylcholine (PC) transporter/transfer protein which is essential to the secretary pathway and to viability as reported by Bankaitis, V., et al., *Nature* 347:561 (1990), the disclosure of which is incorporated herein by reference. Deletion of the yeast SEC14 gene in an otherwise wild type cell is lethal and inactivation of the SEC14 gene product in a temperature-sensitive (sec14$^{ts}$) mutant leads to arrest of the secretory pathway at the late Golgi stage as reported by Novic, P., et al., *Cell* 21:205 (1980), the disclosure of which is incorporated herein by reference. Analysis of suppressors that permit the sec14$^{ts}$ mutant to grow at the restrictive temperature led to the discovery that mutations in the cytidine-diphosphatecholine (CDP-choline) pathway for phosphatidylcholine (PC) biosynthesis (see, FIG. 1) suppress the sec14 mutant phenotype, allowing wild type growth even in strains carrying a total deletion of the SEC14 gene as reported by Cleves, A., et al. (1991).

The CDP-choline pathway, first described by Kennedy, E. P., et al. *J. Biol. Chem.* 222:193 (1956), the disclosure of which is incorporated herein by reference, and also known as the Kennedy pathway, is one of two routes for synthesis of PC in eukaryotic cells, including yeast. The second route for synthesis of PC, originally reported by Bremer, J., et al., *Biochim. Biophys. Acta.* 37:173 (1960), the disclosure of which is incorporated herein by reference, involves methylation of phosphatidylethanolamine (PE). Yeast cells can utilize either the CDP-choline or the PE methylation pathway, or a combination of the two, for net PC synthesis as reported by Griac, P., et al., *J. Biol. Chem.* 271:25692 (1996), the disclosure of which is incorporated herein by reference. (See, FIG. 1). Deletion of the genes in the CDP-choline pathway is not lethal in yeast and appears to have little effect on growth as reported by Griac, P., et al., and McMaster C. P. , et al. *J. Biol. Chem.* 269:14776 (1994), the disclosure of which is incorporated herein by reference. It has been widely assumed that the CDP-choline pathway in yeast functions largely for the utilization of exogenous choline. However, recent studies have suggested that the CDP-choline pathway contributes substantially to PC biosynthesis even in the absence of exogenous choline. See, McMaster, C. R., et al., *J. Biol. Chem.* 269:14776 (1994); McDonough, V. M., et al., *J. Biol. Chem.* 270(32):18774 (1995); and McGee, T. P., et al., *J. Cell. Biol.* 124:273 (1994), the disclosures of which are incorporated herein by reference. In the absence of exogenous choline, the yeast cell synthesizes PC predominantly via methylation of PE. Conversely, yeast cells can survive the complete and simultaneous deletion of the genes encoding the two phospholipid methyltransferases that carry out the three-step conversion of PE to PC, provided choline is supplied in the growth medium as reported by Summers, E. F., et al., *Genetics* 120:909 (1988), the disclosure of which is incorporated herein by reference.

However, deletions of the genes encoding enzymes in either of these two pathways result in subtly different phenotypes. For example, the deletion of either of the phospholipid methyltransferases does not suppress the sec14 growth phenotype as reported by Cleves, A., et al., *Cell* 64:789 (1991a) and Cleves, A., et al., *Trends Cell. Bio.* 1:30 (1991b), the disclosures of which are incorporated herein by reference. However, such mutants are unable to repress the INO1 gene that encodes inositol-1-phosphate synthase (see, FIG. 1) in response to exogenous inositol, unless PC biosynthesis is restored via the CDP-choline pathway. See, Summers, E. F., et al. (1988), and McGraw, P., et al., *Genetics* 122:317 (1989), the disclosure of which is incorporated herein by reference. And while the deletion of genes encodes enzymes of the CDP-choline pathway does not affect INO1 regulation in response to inositol (ee, Griac, P., et al. (1996)), such mutants suppress the sec14 phenotype (see, Cleves, A., et al. (1991a) and (1991b)).

The INO1 gene is the most highly regulated of a set of genes that encode enzymes of phospholipid biosynthesis that are subject to complex coordinate control. All these genes contain a conserved promoter element, UAS$_{INO}$, that includes within it the canonical binding site, CANNTG, for transcription factors of the basic helix-loop-helix class as reported by Paltauf, F., et al., *The Molecular and Cellular Biology of Yeast Saccharomvces* (Broach, J., et al. eds.) Vol. II, pp. 415–500, Cold Spring Harbor Laboratory Press, Plainview, N.Y. (1992), and Bachhawat, N., et al., *J. Biol. Chem.* 270:25087 (1995), the disclosures of which are incorporated herein by reference.

There remains a need, however, for methods to control PC turnover and INO1 regulation in vivo in yeast in order to produce inositol and choline and other inositol- and choline-containing metabolites as well as phosphatidylinositol and phosphatidylcholine. There also remains a need for an improved test for detecting phospholipase D activity and the resulting choline in yeast cultures and a variety of other cell cultures.

According to the present invention, the identification of the metabolic signal (phosphatidic acid (PA)) for derepression of phospholipid biosynthesis in combination with the use of yeast strains which contain mutations that block PC biosynthesis and which are also mutated in their PI/PC transfer protein, SEC14, result in yeast strains that can produce enhanced amounts of inositol and choline as well as other phospholipid metabolites economically. The present invention also provides a means of detecting phospholipase D-mediated or other turnover of PC in vivo via a plate assay for choline excretion.

SUMMARY OF THE INVENTION

Accordingly, it is a primary object of the present invention to determine the signal for derepression of phospholipid biosynthesis and thereby to control production of phospholipids and phospholipid metabolites.

Another object of the present invention is to provide a method for increased production of choline and inositol, choline and inositol metabolites, choline- and inositol-containing phospholipids in yeast, by increasing phosphatidylcholine (PC) turnover in the yeast which is accompanied by, and which can be detected by increased choline excretion.

Another object of the present invention is to provide a method for detecting turnover of phosphatidylcholine (PC) in vivo which results in simultaneous production of phosphatidic acid (PA) and free choline in yeast.

Yet another object of the present invention is to provide a plate assay method for detecting choline excretion in yeast.

Still another object of the present invention is to produce yeast strains having predetermined concentrations of inositol and choline, inositol and choline metabolites, and inositol- and choline-containing phospholipids.

Another object of the present invention is to produce yeast strains in which the production of inositol and choline, inositol and choline metabolites, and inositol- and choline-containing phospholipids can be controlled or "switched on" at will.

Yet another object of the present invention is to provide a method for substantially increased production of inositol and choline.

Another object of the present invention is to provide a method for economical production of inositol and choline.

These and other objects of the present invention are achieved by one or more of the following embodiments.

In one aspect, the invention features a method for increased production of choline and inositol, choline and inositol metabolites, and choline and inositol-containing phospholipids in yeast, comprising the step of increasing phosphatidylcholine (PC) turnover in the yeast.

In a preferred embodiment, the increasing step comprises culturing a yeast strain carrying a mutation in the SEC14 gene of the yeast and a mutation in at least one gene of the Kennedy pathway of the yeast.

In another aspect, the invention features a plate assay for detecting choline excretion from phosphatidylcholine (PC) turnover in yeast growing on a plate, comprising detecting the choline excretion of the yeast strain by visualizing the growth of a choline auxotrophic strain placed onto the plate with the yeast.

Other features and advantages of the invention will be apparent from the following description of the preferred embodiment, and from the claims.

DESCRIPTION OF THE DRAWINGS

FIGS. 6A–6E are graphs showing phospholipid turnover as a function of time or growth temperature. Strains were grown to mid-logarithmic phase in I$^-$ media supplemented with 10 μCi [$^{32}$P]orthophosphate/ml, as described in Table III. The starting phospholipid compositions were identical to those shown in Table III for each respective strain and growth conditions. The data shown in FIGS. 6A, 6B, and 6C represent the relative percentages of the total label retained in each phospholipid species (wild type, SEC14 cki1, sec14$^{ts}$ cki1, respectively). In FIGS. 6A–6C, phosphatidylinositol (PI); phosphatidylcholine (PC); phosphatidylethanolamine (PE); phosphatidylserine (PS); and phosphatidic acid (PA) are represented. "Other" lipids include cytidinediphosphate (CDP-DG), phosphatidylmonomethylethanolamine (PMME), phosphatidyldimethylethanolamine (PDME), cardiolipin (CL), and lipids retained near the origin. The ratio of phosphatidylinositol (PI) to phosphatidylcholine (PC) (FIG. 6D) was calculated from the relative percentage of [$^{32}$P] label associated with PI vs. PC. Label associated with sphingolipid is depicted in FIG. 6E for wild type and sec14$^{ts}$cki1.

FIGS. 8A–8D depict the sec14$^{ts}$ cki1 strain shifted to: (FIG. 8A) I⁺ media at 25° C.; (FIG. 8B) I⁻ media at 25° C.; (FIG. 8C) I⁺ media at 37° C.; and (FIG. 8D) I⁻ media at 37° C. FIGS. 8E and 8F represent the sec14$^{ts}$CKI1 strain shifted to (FIG. 8E) I⁺ media at 37° C., and (FIG. 8F) I⁺ media at 37° C. FIGS. 8G and 8H depict the wild type (SEC14 CKI1) strain shifted to (FIG. 8G) I⁺ media at 37° C., and (FIG. 8H) I⁻ media at 37° C.

DETAILED DESCRIPTION OF THE INVENTION

I. DEFINITIONS

As used herein, "turnover" means catabolism or degradation of a molecule or metabolite such as, for example, phosphatidylcholine in yeast.

"Metabolic signal" means the metabolite that causes derepression of the coordinately controlled phospholipid biosynthetic genes, in the present invention, phosphatidic acid (PA) or a closely related metabolite.

"Plate assay" means a method for assaying choline resulting from phospholipase D activity and/or phosphatidylcholine (PC) turnover which is useful for studies of signal transduction.

"CDP-choline pathway" and "Kennedy pathway" refer to an alternate pathway for making phosphatidylcholine (PC) other than through the methylation of phosphatidyethanolamine (PE) in all eukaryotic cells, for example, yeast. Blockage of the CDP-choline pathway such as by the introduction of the cki1 mutation or other mutation with the same effect results in choline excretion. In instances when the cki1 mutation is combined with the sec14 mutation, the choline excretion is even greater.

"Permissive and nonpermissive temperatures" refer to the temperatures at which a temperature sensitive gene product is functional (permissive) or nonfunctional (nonpermissive). For example, the protein product encoded by the sece4ts allele is nonfunctional at 37° C., thereby causing an increase in choline excretion when combined with a mutation in one of the Kennedy pathway genes.

II. METHODS

According to the present invention, the role of phosphatidylcholine (PC) turnover in INO1 gene regulation has been investigated and methods are provided herein for controlling, i.e., "turning on/turning off" phospholipid biosynthesis in yeast, preferably baker's yeast (*Saccharomyces cerevisiae*). The present invention is based on the discovery of the metabolic signal/indicator for derepression of coordinately regulated phospholipid biosynthetic genes (e.g., INO1) and the means for controlling and utilizing such a metabolic signal/indicator. According to the present invention, it has been found that phophatidic acid (PA) or a closely related metabolite controls production of inositol and inositol-containing phospholipids and other coordinately regulated phospholipid biosynthetic genes. At the same time, it has been found that production of each molecule of PA leads to production of a molecule of free choline. Thus, the present methods leads to controlled production of the two nutrients, choline and inositol, as well as phospholipids and other compounds, such as choline phosphate. Choline and inositol are consumed by humans and animals as a food supplement.

Figure 1:
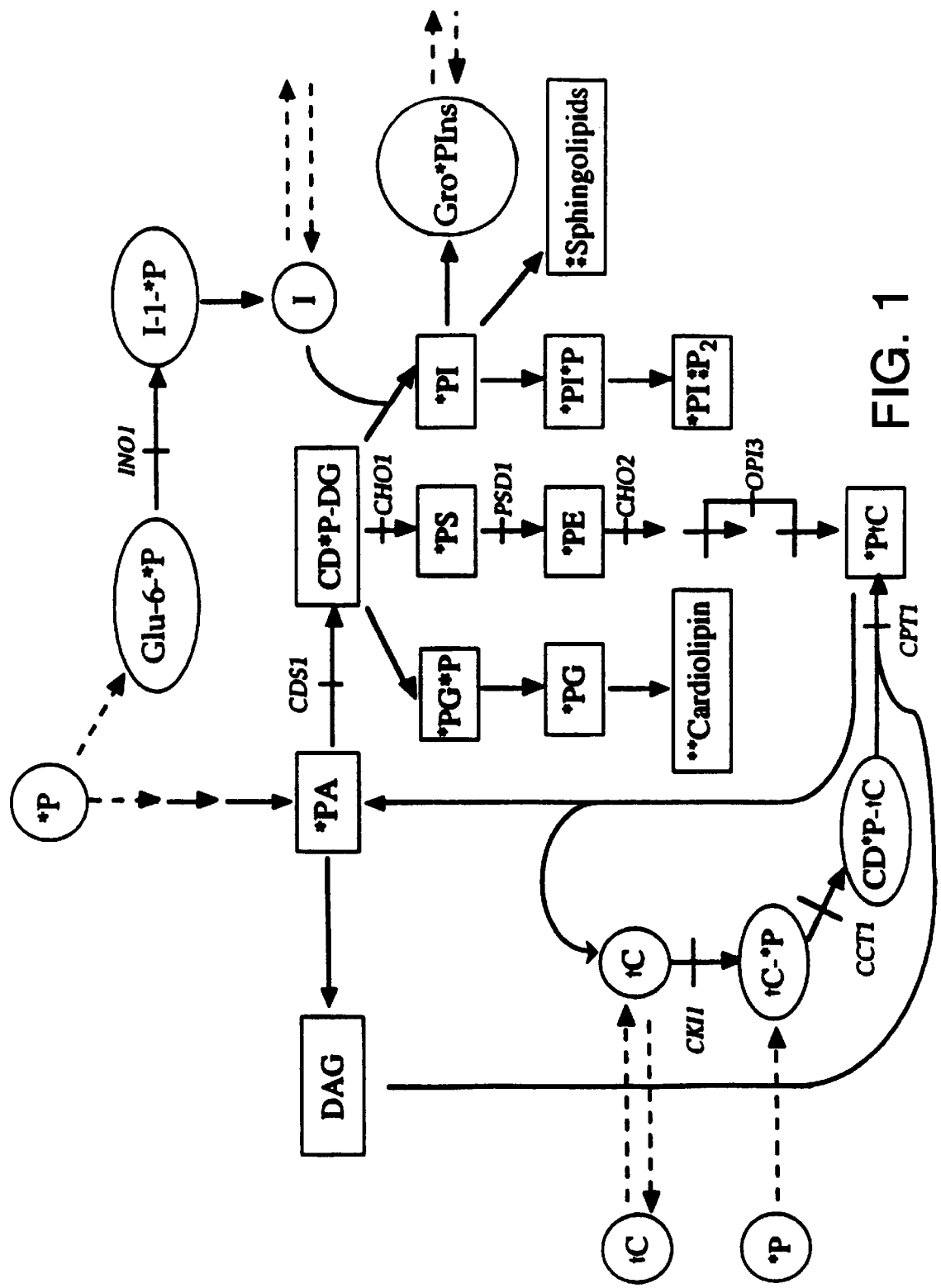
FIG. 1 is a diagram of $^{32}$P-H$_3$PO$_4$ and $^{14}$C-choline labelling routes in S. Cerevisiae. Labelled phosphorous ($^{32}$P) is represented by *P and labelled choline ($^{14}$C) is represented by †C. Water-soluble molecules which can be taken up from media are circled (I, inositol; Gro*PIns, glycerophosphoinositol). Intracellular water-soluble metabolites are shown in ovals (I-1-*P, inositol-1-phosphate; Glu-6-*P, glucose-6-phosphate; †C-*P, choline-phosphate; CD*P-†C, cytidine diphosphate-choline). Lipids are shown in rectangles (DAG, diacylglycerol; *PA, phosphatidic acid; CD*P-DG, cytidine diphosphate-diacylglycerol; *PG*P, phosphatidylglycerol phosphate; *PG, phosphatidylglycerol; *PS, phosphatidylserine; *PE, phosphatidyl-ethanolamine; *P†C, phosphatidylcholine; *PI, phosphatidylinositol; *PI*P, phosphatidylinositol phosphate; *PI*P$_2$, phosphatidylinositol biphosphate. Solid lines represent routes of metabolic conversion. Dashed lines indicate potential flux across the plasma membrane.

The present invention specifically provides a method for detecting phospholipase D (PLD)-mediated turnover of phosphatidylcholine (PC) in vivo. This turnover results in simultaneous production of PA and free choline as shown in FIG. 1. A method is also provided for detecting choline produced by non-PLD mediated routes.

The present invention also provides methods for increasing phosphatidylcholine (PC) turnover in yeast. Such turnover can be accomplished in several ways, such as, for example, chemical means and genetic means. PC turnover can be activated chemically, for example, by addition of suitable detergent to the culture medium. Other means for increasing PC turnover in yeast are also contemplated by the present invention. The example below utilizes genetic means to cause PC turnover in yeast.

An aspect of the present invention involves:

blocking the pathway for reutilization of free choline (CDP-choline pathway in FIG. 1) by introducing, for example, a cki1, cct1, or cpt1 mutation into a strain that does not allow PI/PC exchange such as a sec14 strain, more particularly the sec14$^{ts}$ strain; and utilizing a choline-requiring strain such as, for example, cho2 opi3, to detect choline output in a bio-assay that allows one to make semi-quantitative comparisons of choline output for assaying phospholipase D activity.

Thus, the present invention encompasses a method for switching on accelerated PLD-mediated turnover of PC by combining a mutation in the PI/PC transporter protein (Sec14p) with a mutation in the CDP-choline pathway. When, for example, a temperature sensitive allele of sec14 is used, the switch to accelerated turnover can be achieved by shifting the temperature of a strain having the genotype sec14$^{ts}$ cki1, sec14$^{ts}$cct1, or sec14$^{ts}$ cpt1, or other genotype with this property. However, a temperature sensitive allele of sec14 is not a requirement of the present invention. A mutation in the sec14 allele is not lethal when it is present in the background of a cki1, cct1 or cpt1 mutation. Thus, the present invention is not limited to the sec14$^{ts}$ allele.

A result of the accelerated PC turnover is the production of free choline which is excreted into the medium if the sec14$^{ts}$ allele is used in combination with the cki1 mutation. However, use of the cct1 or cpt1 mutants allows production of high intracellular levels of choline phosphate and/or cytidinediphosphate (CDP)-choline, respectively, as well as free choline.

Another result of accelerated PC turnover leads to PA production which, in turn, leads to immediate "switching on" of transcription of the INO1 gene, the structural gene for inositol-1-phosphate and all other coregulated genes of phospholipid biosynthesis. This in turn leads to excretion of inositol, increased production of the inositol-containing phospholipids such as phosphatidylinositol (PI), phosphatidylinositol phosphate (PIP), phosphatidylinositol biophosphate (PIP$_2$) and inositol-containing sphingolipids.

According to the present invention the metabolic signal is detected by in turn detecting phosphatidylcholine turnover by which PA and choline are produced via a plate assay for choline excretion as described herein. Thus, by controlling the levels of PA in yeast, the genes for inositol, inositol-containing phospholipids, and free choline can be controlled or "switched on" at will. As a result, production of inositol and inositol-containing metabolites is substantially increased compared to existing yeast strains. Also according to the present invention a plate assay for choline excretion is provided to detect PC turnover and PLD activity that can be used in investigations of signal transduction.

When Sec14p is inactivated, PC turnover is increased, the INO1 gene is derepressed, and the Opi⁻ phenotype is produced, but only if the CDP-choline pathway is simultaneously blocked, as is the example of the sec14$^{ts}$ cki1 strain shifted to 37° C. In contrast, the Opi⁻ phenotype in the cho1, cho2 and opi3 mutants is eliminated and INO1 repression in response to inositol is restored only when the mutant cells are able to make PC using the CDP-choline pathway. These two apparently distinctly different metabolic conditions, one involving increased PC turnover in the sec14$^{ts}$ cki1 strain, and the other involving diminished PC biosynthesis, as in the cho1, cho2 or opi3 strains, both result in Opi⁻ phenotypes and, therefore, must have something in common.

It is believed that the common metabolic factor in the mutant strains that exhibit an Opi⁻ phenotype, is not reduced PC biosynthesis as had been previously hypothesized, but rather it is the cellular balance in the relative rate of production versus utilization of a phospholipid precursor early in the pathway leading to PC biosynthesis. According to the present invention, an Opi⁻ phenotype will be produced and INO1 will be derepressed under conditions in which the specific precursor that generates the metabolic signal for derepression is being made at a rate that is in excess of its utilization. In the sec14$^{ts}$ cki1 strain shifted to the restrictive temperature, two precursors, PA and choline, are being produced by PC turnover. It has been shown previously that free choline is not responsible for the metabolic signal. According to the present invention, it is believed that the signal is being generated by PA or a closely related metabolite. All mutants with a structural gene block in the pathway that leads from PA to PC biosynthesis (i.e., in FIG. 1, PA→CDP-DG→PS→PE→→→PC) have an Opi⁻ phenotype. According to the present invention, the Opi⁻ phenotype in these mutants is the result of "damming up" of upstream metabolites. When this occurs, the cellular response is depression of all of the coordinately regulated enzymes containing UAS$_{INO}$, including all of the enzymes in the pathway leading from PA→PC, all of which catalyze reactions that make use of metabolites downstream of PA. The derepression of these downstream enzymes would tend to eliminate any "damming-up" of precursors such as PA in wild type cells. However, in each of the mutants defective in PC biosynthesis, there is a metabolic bottleneck which cannot be relieved by derepressing the system.

Thus, the common feature in the sec14$^{ts}$cki1 strain shifted to the restrictive temperature and the mutants with defects in the reaction series: PA→CDP-DG→PS→PE→→→PC is, according to the present invention, the build-up of an early precursor in this reaction series. This model predicts that any structural gene mutant with a defect in the sequence of reactions culminating in PC biosynthesis via PE methylation that exhibits an Opi⁻ phenotype must have a lesion that lies downstream from the metabolite that produces the signal for INO1 derepression. The mutant furthest upstream from PC that has been shown to date to have the Opi⁻ phenotype is CDG1 (Klig, L. S., et al., *J. Bacteriol.* 170:1878 (1988), the disclosure of which is incorporated herein by reference). The cdg1 mutant was shown to be defective in the structural gene for cytidinediphosphate diacylglycesol (CDP-DG) synthase (CDS1) See, Shen, H., et al., *J. Biol Chem.* 271:789 (1996), the disclosure of which is incorporated herein by reference. Furthermore, recent evidence shows that derepression of INO1 and coregulated genes containing UAS$_{INO}$ in their promoters are highly correlated to the level of CDP-DG synthase. According to the model of the present invention, the metabolite responsible for generating the regulatory response cannot be CDP-DG, which is downstream of the genetic block in the cdg1 mutant. Accordingly, the metabolite must be PA or a metabolite upstream of PA. Consistent with this model, it is believed that the excessive turnover of PC via a PLD mediated route in the sec14$^{ts}$ cki1 mutant produces PA more rapidly than the cell can process it. Thus, the metabolic balance is tilted, not by slowing the rate of flux through downstream steps as in the cdg1, cho1, cho2 or opi3 mutants, but by accelerating input of PA. Since PA is a very transient precursor which is rapidly used in downstream reactions, the sensing mechanism that produces the signal must be very sensitive to the flux of metabolites in the pathway.

In the wild type cells, according to the present invention, the addition of inositol to the growth medium leads to repression of INO1 and coregulated genes because it causes an increase in the rate of utilization of PA in de novo lipid synthesis. Indeed, in the presence of inositol, the overall rate of $^{32}$P incorporation into phospholipids is increased in the wild type strain (Table IV below). Virtually all the lipids labelled in a 30 minute pulse (Table IV) are made via the PA intermediate with the exception of the $^{32}$P labelling of PC that occurs via the PA intermediate with the CDP-choline pathway (FIG. 1). Thus, in a 30 minute pulse, the proportion of label that is actually recovered as PA is but a small percentage of the total $^{32}$P that passes through the PA branchpoint. However, PA produced by PLD mediated turnover will not be labelled proportionally and, thus, $^{32}$P pulse labelling will underestimate the total rate of phospholipid synthesis in strains, such as sec14$^{ts}$ cki1 at 37° C., in which phospholipid turnover is increased.

In the wild type cells, the model of the present invention predicts that the early precursors such as PA are made de novo somewhat in excess of their rate of utilization when inositol is absent from the medium. The build-up of these precursors generates a signal that results in derepression of the INO1 gene, leading to inositol production which is used in PI production, thereby drawing on the pool of early precursors such as PA. When exogenous inositol is present, the rate of PI production increases sufficiently to lower pools of PA and other precursors to the point of repressing the system. Thus, inositol availability affects the overall rate of phospholipid precursor output vs. input in wild type cells. This results in repression, however, only when the other major branches of the pathways that utilize PA and other early precursors are unimpeded and/or when rates of lipid turnover contributing to the inflow of PA are normal. In wild type cells, the presence of choline leads to a further degree of repression, but only if inositol is already present (see, Paltauf, F., et al., (1992)). In cho1, cho2, and opi3 mutants, the addition of choline to the growth medium also restores the metabolic system to a state where it can be repressed in response to inositol (see, e.g., McGraw, P., et al. (1989). When choline is supplied to a cho1cho2, or opi3 mutant, major net synthesis of PC occurs via the CDP-choline route using DAG as an intermediate in lipid biosynthesis (FIG. 1). DAG is derived from PA (FIG. 1) and, thus, choline supplementation of these mutants relieves the precursor "dam" that keeps PA levels high by opening a "sluice gate" via an alternative pathway branchpoint, downstream of PA.

The model of the present invention also explains why genes containing UAS$_{INO}$ are repressed (cannot derepress) in stationary phase whether or not inositol is present. If major cellular metabolites (i.e, carbon or phosphorous, etc.) are limiting, PA and other early precursors will not be made de novo and there will be no build-up of such precursors to be relieved by turning on the INO1 gene and other enzymes of phospholipid metabolism. Thus, it was observed that all of the strains tested showed leveling-off of the INO1 lacZ reporter construct in stationary phase with the exception of sec14$^{ts}$ cki1 at 37° C. At 37° C., the sec14$^{ts}$ cki1 strain continued to express the INO1 reporter construct, consistent with the idea that there is ongoing production of PA via lipid turnover which, according to the present model, could cause derepression of INO1, even in stationary phase.

In sum, the unifying model for the methods of the present invention is that the metabolic signal in S. cerevisiae that communicates via the OPI1 gene product with the INO2 and INO4 gene products, is a metabolite in an early step of phospholipid biosynthesis. It is believed that the signal is phosphatidic acid (PA) itself, or a metabolite closely related to PA.

In this model, the transcription of $UAS_{INO}$-containing genes will be high when conditions favor high levels of PA. PA levels can be influenced by at least four complex metabolic factors.

1. General cellular metabolic conditions, including levels of basic metabolites like phosphorus and carbon. When general metabolic activity is low, as in stationary phase, PA levels are low and the system is in the repressed state.
2. Availability of inositol during active growth. When inositol is added to the growth medium of actively growing cells, it causes an immediate shift in the pattern of phospholipid biosynthesis. The rate of synthesis of PI rises at the expense of the upstream precursors, PA and CDP-DG. PA and CDP-DG levels drop and the coregulated genes are repressed. Choline, when added by itself in the absence of inositol, enters a different point in the pathway and draws initially on reserves of DG (FIG. 1). However, DG and PA pools appear to be related through an as yet undefined equilibrium. Thus, under conditions where the PA pools are already depleted by the presence of inositol, choline does have an effect and causes further repression. Choline also has a major effect on regulation in those mutants having a block in the synthesis of PC via PE methylation as discussed below.
3. Overall metabolic flow in the pathway leading from PA to PC biosynthesis. In general, a genetic lesion that institutes a significant block in the de novo pathway for PC biosynthesis: PA→CDP-DG→PS→PE→→→PC causes a build-up of precursors, including PA, upstream from the lesion. This leads, in turn, to high level derepression of INO1 and other coregulated genes. However, if a precursor such as choline is added to the growth medium, it can alleviate the build-up of precursors by drawing on DG for the synthesis of PC via the Kennedy pathway. Under these conditions, the overexpression of INO1 and other coregulated genes is alleviated and the cells become capable of repression in response to inositol.
4. Phospholipid turnover. Phospholipase D (PLD)-mediated turnover of PC produces PA and free choline. The PA produced by this route can, under some circumstances, constitute a major component of the total PA pool. Thus, if PLD-mediated turnover is abnormally high, it can lead to unscheduled derepression of the genes containing $UAS_{INO}$. This, in turn, can lead to an inositol excretion phenotype. The other major product of PLD-mediated turnover is choline, which, under certain circumstances (i.e., a block such as cki1 in the CDP-choline pathway), is excreted from the cell. It is believed that this is the explanation for the phenotypes that were observed in the sec14$^{ts}$ cki strain at the restrictive temperature.

In the following example, sec14$^{ts}$ cki1 and sec14$^{ts}$ in combination with other mutations in the CDP-choline/Kennedy pathway in I$^-$C$^-$ media at the restrictive temperature of 37° C. results in PC turnover and concomitant overproduction of choline and inositol and other metabolites. Additionally, a plate assay for choline excretion is provided for detecting the choline byproduct of PC turnover.

EXAMPLE

Yeast Strains. Yeast strains used are shown in Table I below. All strains were obtained as gifts from the sources indicated and are available upon request. Additionally, all the sec14 cki1, sec14 cct1, and sec14 cpt1 mutants and individual strains can be made according to procedures well known in the art and are described by McGee, T. P., et al., *J. Cell. Biol.* 124:273 (1994), the disclosure of which is incorporated herein by reference. The Saccharomyces Genome Data Base (http://genome/www.stanford.edu/saccharomyceso) contains the entire sequence of the Saccharomyces genome, including these genes. The cho2 opi3 strain can be made according to procedures well known in the art as described by Summers, E. F., et al., *Genetics* 120:909 (1988), the disclosure of which is incorporated herein by reference. AID can be made according to procedures well known in the art.

TABLE 1

Yeast Strains

| Strain | Genotype |
|---|---|
| wt (SEC14 CKI1)[1] | MATa ura3-52, his3-200, lys2-801 |
| sec14$^{ts}$ CKI1[1] | MATa ura3-52, his3-200, lys2-801, sec 14-1$^{ts}$ |
| sec14$^{ts}$ cki1[1] | MATa ura3-52, his3-200, lys2-801, sec14-3$^{TS}$, cki1-281::HIS3 |
| SEC14 cki1[2] | MATa ura3, his3, lys2, cki1-281::HIS3 |
| AID[2] | MATa/α ade1/ade1, ino1/ino1 |
| cho2 opi3[2] | MATa opi3, leu2, cho2::LEU2 |
| opi1[2] | MATa leu2, his3, opi1::LEU2 |
| sec14 cpt1[1] | MATa ura3, his3, ade2, sec14-1, cpt::LEU2 |
| SEC14 cpt1[3] | MATa his3, trp1, ura3, leu2, cpt::LEU2 |
| sec14 cct1[1] | MATa ura3, his3, lys2, sec14-1, cct |
| SEC14 cct1[1] | MATa can1-100, ade2, his3, leu2, trp1, ura3, cct::URA3 |

[1]Obtained as a gift from V. Bankaitis (University of Alabama, Birmingham, AL) and available upon request.
[2]Obtained from S. Henry (Carnegie Mellon University, Pittsburgh, PA) and available upon request.
[3]Obtained as a gift from R. Bell (Glaxo Wellcome Inc., Research Triangle Park, NC) and available upon request.

Culture conditions. Yeast strains were maintained on YEPD (1% yeast extract, 2% Bactopeptone, 3% glucose) (Difcol Laboratories, Inc., Detroit, Mich.). Chemically-defined synthetic media was prepared as described by Griac, P., et al. (1996). Synthetic medium either lacked inositol (I$^-$) or was supplemented with 75 μM inositol (I$^+$) and/or 1 mM choline (C$^+$) (Sigma Chemical, St. Louis, Mo.).

Yeast transformation. Yeast transformation was performed by the lithium acetate method as reported by Gietz, D., et al., *Nucl. Acids Res.* 20:1425 (1992), the disclosure of which is incorporated herein by reference.

Assay for Opi$^-$ (overproduction of inositol) and Opc$^-$ (overproduction of choline) phenotypes. To test for the Opi$^-$ phenotype (see, Greenberg, M., et al. *Genetics* 100:19 (1982), and Swede, M. J., et al., *Methods in Enzymology: Phospholipid Biosynthesis* (Vance, D. E., et al., eds.) Vol. 29 pp. 21–34 (1992), the disclosures of which are incorporated herein by reference, for a complete method description), strains were patched onto synthetic I$^-$ media and allowed to grow at the indicated temperatures (25° C., 30° C., and 37° C.) for two days. The plates were then sprayed with a suspension of a diploid tester strain (AID), which is homozygous for ino1 and ade1 (Table I), and incubated for another two days.

For the Opc⁻ phenotype, strains were patched onto plates containing synthetic I⁺ or I⁻ medium lacking choline (C⁻), and were allowed to grow at the indicated temperature for two days. The strains were then sprayed with a tester strain, cho2 opi3, (Table I), which is auxotrophic for choline and were incubated for another two days at 30° C. or 37° C. or another three days at 25° C.

β-Galactosidase assay. Each strain was transformed to uracil prototrophy with plasmid pJH359 (-359 to -119 INO1-CYC1-lacI' Z), as described by Lopes, J., et al., *Nucl. Acids Res.*, 19(7):1687 (1991), the disclosure of which is incorporated herein by reference. The transformed strains were grown to midlogarithmic growth phase in I⁺ or I⁻ medium. The β-galactosidase assays were performed as described by Lopes, J., et al. (1991), except that aliquots were removed from the reaction mix at 5, 10 and 15 minutes. For temperature shift experiments, the strains were initially grown in repressing conditions (I⁺ medium) at 25° C., the cultures were filtered, and the cells were used to inoculate separate cultures to be grown at 25° C. or 37° C. in either repressing (I⁺) or derepressing conditions (I⁻). Samples were harvested at intervals and assayed for β-galactosidase activity.

Northern analysis. RNA probes were synthesized from plasmids previously described by Hudak, K. A., et al., *Genetics* 136:475 (1994), the disclosure of which is incorporated herein by reference. Plasmids were linearized with a restriction enzyme and transcribed, in the presence of [$^{32}$P]cytidine 5' triphosphate, using an RNA polymerase as follows (plasmid/restriction enzyme/RNA polymerase): pAB309 Δ/EcoRI/SP6 (TCM1), pJH310/HindIII/T7 (INO1). Transcription was performed according to the manufacturer's protocol for the SP6/T7 Riboprobe Combination System (Promega Corp., Madison, Wis.). The experimental cultures were grown at the indicated temperatures to early logarithmic phase of growth ($OD_{595}$ between 0.2 and 0.25) and RNA was isolated using glass bead disruption and hot phenol extraction, as described by Elion, E. A., et al., *Cell* 39:663 (1984), the disclosure of which is incorporated herein by reference. The TCM1 ribosomal protein gene, which is expressed constitutively with respect to inositol and choline availability, was used as a standard for RNA loading as described by Hirsch, J. P., et al., *Mol. Cell. Biol.* 6(10):3320 (1986), the disclosure of which is incorporated herein by reference. Northern hybridization was performed, visualized by autoradiography, and quantitated with an AMBIS 4000 phosphorimager (AMBIS, Inc., San Diego, Calif.), as described by Griac, P., et al. (1996).

Phosiholipid analysis. To determine steady state phospholipid composition, strains were grown in I⁺ or I⁻ synthetic media containing 10 μCi [$^{32}$P]orthophosphate/ml. The cultures were harvested in mid-logarithmic phase ($OD_{595}$ =0.4–0.6) after five to six generations of growth at the indicated temperature. Labelled lipids were extracted, as described by Atkinson, K. D., et al., *J. Bacteriol.* 141:558 (1980), the disclosure of which is incorporated herein by reference, individual phospholipid species were resolved by two-dimensional paper chromatography, as described by Steiner, M. R., et al., *Biochim. Biophys. Acta* 260:222 (1972), the disclosure of which is incorporated herein by reference, and quantified by liquid scintillation counting. For phospholipid turnover experiments, cells were labelled as described above, harvested, washed twice in fresh media lacking labelled orthophosphate, and suspended at $OD_{595}$ =0.1 under the indicated culture conditions. Aliquots of these cultures were removed at indicated times and phospholipids were analyzed. The rate of phospholipid synthesis in vivo was determined by pulse labelling the cells for 30 minutes with 50 μCi [$^{32}$P]orthophosphate/ml as described by Kelley, M. J., et al. *J. Biol. Chem.* 263:18078 (1988), the disclosure of which is incorporated herein by reference, followed by lipid extraction and separation by paper chromatography, as described above. The amount of [$^{32}$P] phosphate incorporated into sphingolipids was determined by deacylating the extracted lipids and separating the sphingolipids by one-dimensional chromatography, as described by Becker, G. W., et al. *J. Bacteriol.* 142:747 (1980), the disclosure of which is incorporated herein by reference.

Metabolic labelling with $^{14}$C-choline. Strains were grown overnight at the indicated temperatures in I⁻ media containing 1 μci/ml 1,2-$^{14}$C choline (America Radiolabeled Chemicals, St. Louis, Mo.) at a concentration of 10 μM. Cultures were harvested during mid-logarithmic phase, washed twice in fresh non-radioactive media, and suspended at $OD_{595}$=0.1 in I⁻C⁻ media. At the indicated time points, aliquots of the cultures were removed, and the cells were pelleted by centrifugation. The supernatant was saved as the "media" fraction. The cell pellet was processed as described by Atkinson, K. D., et al. (1980) for the extraction of lipids with one addition; following treatment of the cell pellet with TCA to permeabilize the cell membrane, the supernatant and subsequent pellet washes were combined and saved as the "intracellular water-soluble fraction of the cell." This fraction contained the vast majority of the intracellular water-soluble counts as evidenced by the fact that >90% of the counts found in the only other cellular fraction (the lipid fraction) were shown by chromatography to be PC.

Separation of choline-containing water-soluble metabolites. Cation exchange chromatography on Bio-Rex 70 resin (50–100 mesh) (Bio-Rad Laboratories, Richmond, Calif.) was used to separate quantitatively the 1,2-$^{14}$C choline in the aqueous media washes or the TCA extracts from other water soluble 1,2-$^{14}$C choline-containing metabolites, as described by Martin, T. W., *Biochim. Biophys. Acta* 962:282 (1988), the disclosure of which is incorporated herein by reference. The aqueous samples (3 to 5 ml) were neutralized with 1.0M Tris buffer, pH 8.0, as necessary, and applied to a 1 ml Bio-Rex 70 column. The column was then washed with 5 ml $H_2O$, followed by 10 ml 50 mM glycine and 500 mM NaCl, pH 3.0, to elute the choline retained by the resin. The fractions were counted to determine the percentages of various metabolites present.

III. RESULTS

Figure 2:
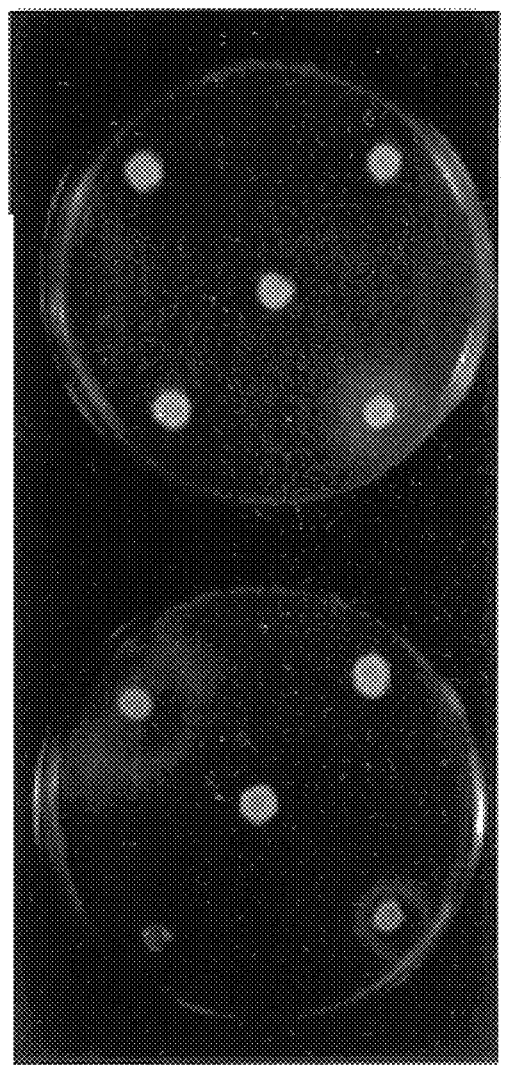
FIG. 2 is a photograph of plate assays at 25° C. and 37° C. showing the overproduction of inositol (Opi-) phenotype. Wild type (wt), sec14 cki1 (sec14, cki1), SEC14 cki1 (cki), sec14$^{ts}$CKI1 (sec14), and opi1 strains were tested. Overexpression and excretion of inositol by strains results in growth of the tester strain as observed by a halo around the strain being tested. The opi1 strain is included as a positive control.
Figure 2:
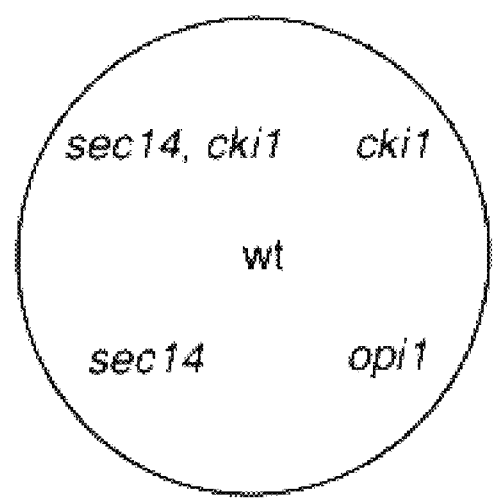
Figure 3A:
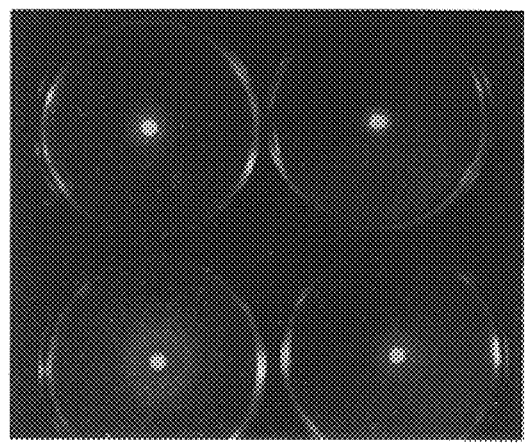
FIGS. 3A–3C are photographs of plate assays at 30° C. and 37° C. showing the overproduction of choline phenotype (Opc-) phenotype. Strains SEC14 cki1 (cki) (FIG. 3A), sec14$^{ts}$cki1 (sec14, cki1) (FIG. 3B), and wild type (wt) (FIG. 3C) were tested as described herein. Excretion of choline results in growth of the tester strain as observed by a halo around the strain being tested.
Figure 3B:
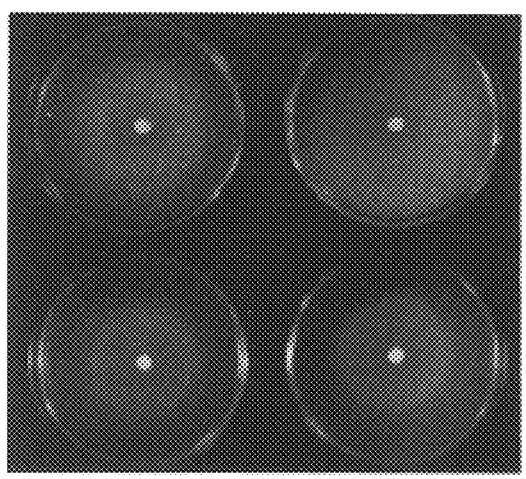
Figure 3C:
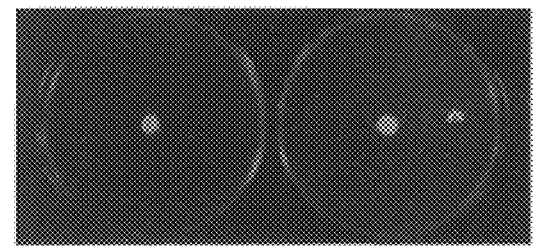

Inositol and choline excretion ohenotvlpe in strains carrying the sec14$^{ts}$ allele in combination with CDP-choline pathway mutations. The overproduction of inositol (Opi⁻) phenotype (FIG. 2) is associated with misregulation of the INO1 gene, as described by Griac, P., et al. (1996); Paltauf, F., et al. (1992); and Greenberg, M., et al. (1982). According to the present invention, a related choline excretion phenotype (FIG. 3) is shown, which is designated as Opc⁻ (overproduction of choline). The Opi⁻ and Opc⁻ phenotypes of the strains used are shown in FIGS. 2 and 3 and are summarized in Table II below. As previously reported by Griac, P., et al. (1996), strains carrying only mutations in the CDP-choline pathway exhibited no Opi⁻ phenotype. However, all of the CDP-choline pathway mutants exhibited the Opc⁻ phenotype to varying degrees. No Opi⁻ phenotype was observed for the strain carrying the sec14$^{ts}$ mutation (but no mutation in the CDP-choline pathway) at its permissive temperature, 25° C., or at 30° C. (Table II)- Strains carrying the sec14$^{ts}$ mutation will be referred to hereafter as sec14$^{ts}$ CKT1 (Table I) because most of the subsequent studies were done with the set of strains carrying combinations of the sec14$^{ts}$ and cki1 mutation. A slight Opc$^-$ phenotype was observed for the sec14$^{ts}$ CKI1 strain, but only in I$^-$ media at 30° C.

At 30° C., a temperature which is still permissive for sec14$^{ts}$, the double mutants containing sec14$^{ts}$ in combination with each of the CDP-choline pathway lesions (i.e., sec14$^{ts}$ cki1; sec14$^{ts}$ cct1; sec14$^{ts}$ cpt1) had an Opc$^-$ phenotype somewhat stronger than the phenotype exhibited by strains carrying only the CDP-choline pathway mutation in question (Table II). At 25°, none of these double mutant strains exhibited an Opi$^-$ phenotype. However, at 37° C., the temperature at which the sec14$^{ts}$ gene product is inactivated, all three double mutants exhibited Opi$^-$ phenotypes, as well as dramatically stronger Opc$^-$ phenotypes than those seen in these same strains at 30° C. or in strains carrying only the respective CDP-choline pathway lesions at any temperature (FIG. 2;

TABLE II

Summary of Opc$^-$ and Opi$^-$ phenotypes
Qualitative assessment of Opc$^-$ (A) and Opc$^-$ (B) phenotypes based upon the size of the growth halo (FIGS. 2 and 3) formed by the relevant tester strain as described in "Example". Strains were grown at the indicated temperatures in I$^-$ or I$^+$ medium for the Opc$^-$ test and in I$^-$ medium for the opi$^-$ test.

A. Opc$^-$ phenotypes

| Strain | 25° C. I$^-$ | 25° C. I$^+$ | 30° C. I$^-$ | 30° C. I$^+$ | 37° C. I$^-$ | 37° C. I$^+$ |
|---|---|---|---|---|---|---|
| wt (SEC14 CKI1) | − | − | − | − | − | − |
| sec14$^{ts}$ CKI1 | − | − | +/− | − | ng | ng |
| SEC14 cki1 | + | + | + | + | + | + |
| sec14$^{ts}$ cki1 | + | + | ++ | ++ | +++ | +++ |
| SEC14 cpt1 | − | − | +/− | − | +/− | − |
| sec14$^{ts}$ cpt1 | − | − | + | + | + | ++ |
| SEC14 cct1 | + | + | + | + | + | + |
| sec14$^{ts}$ cct1 | + | + | ++ | ++ | ++ | +++ |

B. Opi$^-$ phenotypes

| Strain | 25° C. | 30° C. | 37° C. |
|---|---|---|---|
| wt | − | − | − |
| sec14$^{ts}$ CKI1 | − | − | ng$^b$ |
| SEC14 cki1 | − | − | − |
| sec14$^{ts}$ cki1 | − | + | + |
| SEC14 cpt1 | − | − | np$^a$ |
| sec14$^{ts}$ cpt1 | − | +/− | +/− |
| SEC14 cct1 | − | − | np |
| sec14$^{ts}$ cct1 | − | + | + |

$^a$np, not performed
$^b$ng, no growth

Choline metabolism. In the absence of exogenous choline supplementation, yeast cells make PC primarily via methylation of PE (FIG. 1). The choline excretion phenotype of the CDP-choline pathway mutants (FIG. 3) suggests that choline is being produced in the de novo synthesis of PC via methylation of PE, followed by PC, turnover (see, metabolic pathway, FIG. 1). Equivalent turnover presumably occurs in the normal course of lipid metabolism in wild type strains, but the choline is rapidly reutilized via the CDP-choline pathway without escaping from the cell. The increase in choline excretion at the restrictive temperature in the double mutants, carrying the sec14$^{ts}$ allele in combination with one of the CDP-choline pathway mutations, therefore, suggests that accelerated turnover of PC is occurring.

To test this idea, the wild type, SEC14 cki1, sec14$^{ts}$ CKI1 and sec14$^{ts}$ cki1 strains were labelled with $^{14}$C choline in I$^-$C$^-$ medium. $^{14}$C choline is incorporated into PC via the CDP-choline pathway (FIG. 1), but strains carrying the cki1 mutation have very reduced capacity to incorporate $^{14}$C choline into PC. It was found that incorporation of $^{14}$C choline into PC in SEC14 cki1 and sec14$^{ts}$ cki1 strains was approximately 13% of the wild type level, comparable to previous reports for cki1 strains as described by Griac, P., et al. (1996) and Hosaka, K., et al., J. Biol. Chem. 264:2053 (1989), the disclosure of which is incorporated herein by reference. Analysis of the chloroform soluble label extract from all four strains labelled at 25° C. (i.e., wild type, sec14$^{ts}$ CKI1, SEC14 cki1 and sec14$^{ts}$ cki1) demonstrated that >90% of the label was associated with PC.

Figure 4C:
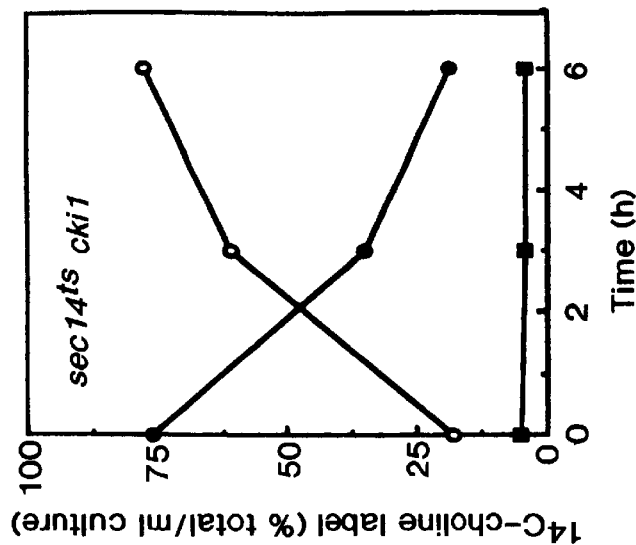
FIGS. 4A–4C show, respectively, phosphatidylcholine turnover in wild type (wt), SEC14 cki1, and sec14$^{ts}$cki1 strains at 37° C. as a function of time. Strains were grown in I$^-$ medium containing 1μ Ci/ml $^{14}$C-choline to midlogarithmic phase. Data are expressed as a percentage of total label recovered in each fraction at each time point after the shift to unlabelled medium: culture medium (○), cellular water-soluble fraction (■), and cellular chloroform-soluble fraction (●). Data are the average of two independent experiments.

To study PC turnover, $^{14}$C choline-labelled cells were shifted to unlabelled medium and the fate of the label was charted. The pattern of label transfer between the lipid soluble pool, the intracellular water soluble pool, and the medium following the shift to unlabelled medium is shown for three strains (wild type; SEC14 cki1 and sec14$^{ts}$ cki1) at 37° C. in FIGS. 4 and 5. All four strains were tested in this fashion at 25° C. as well (data not shown), and only two patterns of turnover were observed. The "wild type" pattern was exhibited by both wild type and sec14$^{ts}$ CKI1 at 25° C. and by wild type at 37° C. (FIG. 4A). The "cki1" pattern was exhibited by both SEC14 cki1 and sec14$^{ts}$ cki1 strains at 25° C. and by the SEC14 cki1 strain at 37° C. (FIG. 4B).

Figure 4B:
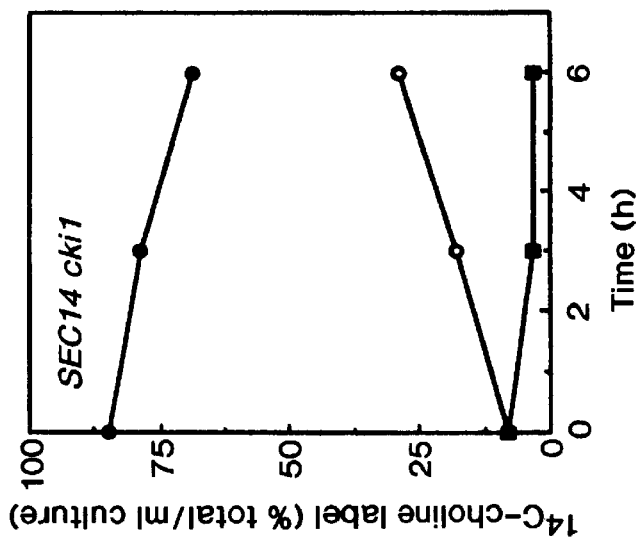
Figure 4A:
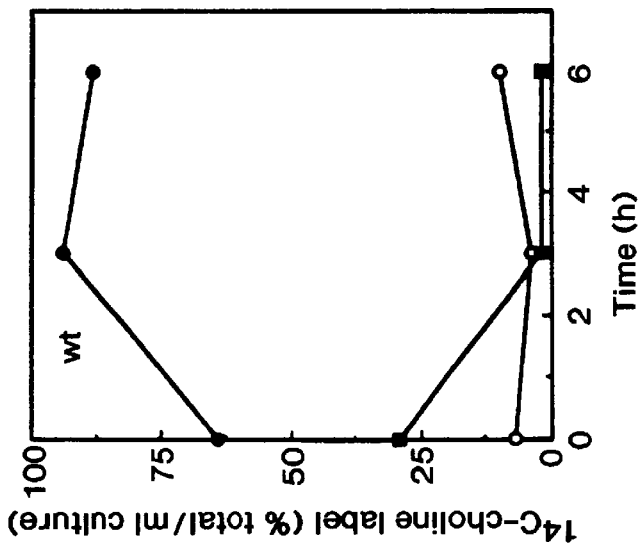
Figure 5:
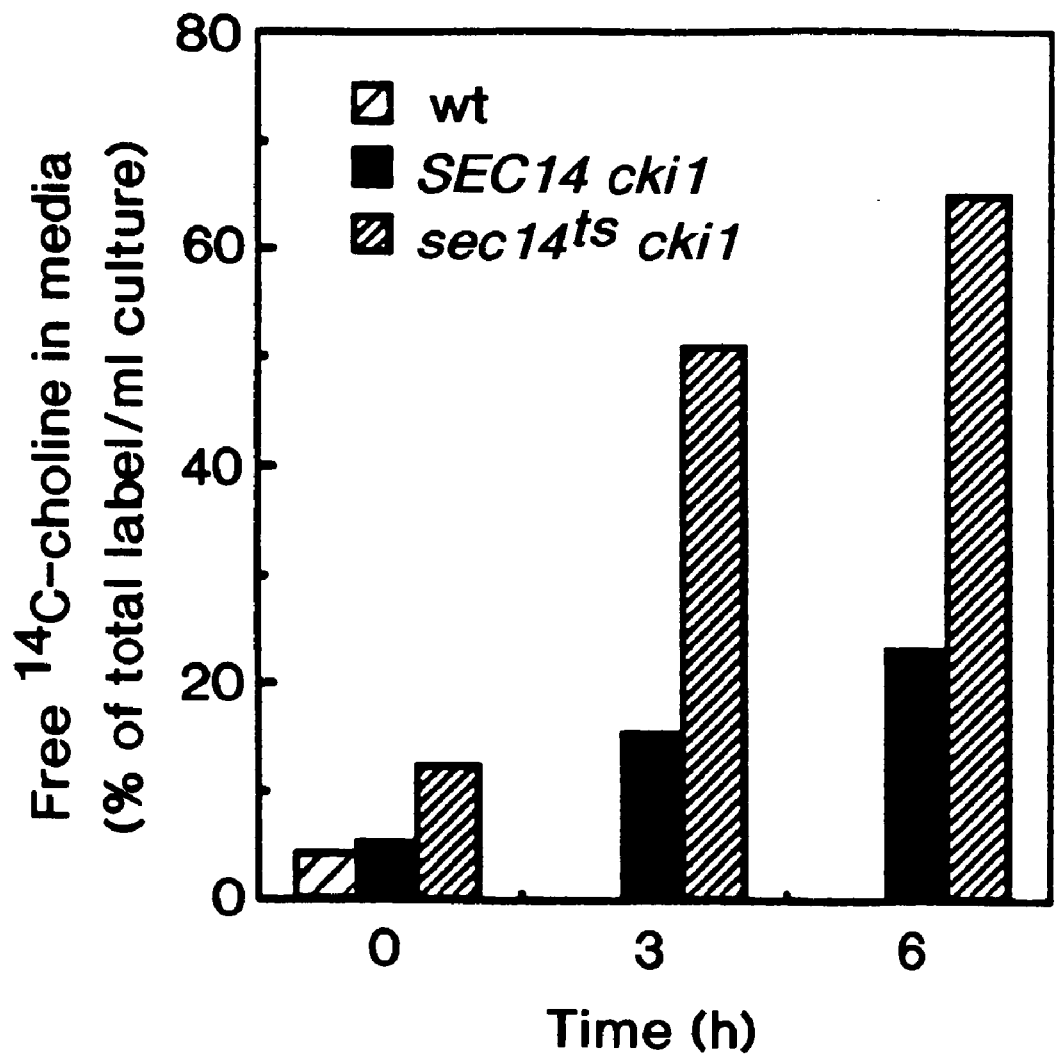
FIG. 5 is a graph showing choline accumulation in the medium of wild type (wt), SEC14 cki1, and sec14$^{ts}$cki1 cultures at 37° C. $^{14}$C-choline was separated from other $^{14}$C-choline-containing metabolites by cation exchange chromatography as described in herein. Data are presented as the percentage of total radioactivity recovered at each point in each strain, and are the average of two independent experiments.

In strains exhibiting the "wild type" pattern of choline metabolism (i.e., the wild type strain at both 25° C. and 37° C. and sec14$^{ts}$ CKI1 only at the permissive temperature of 25° C.), the cells at the time of transfer to unlabelled medium had a significant amount (19–29%) of their cellular $^{14}$C label in a water soluble intracellular pool (FIG. 4A). The remaining cellular label was lipid associated. A small amount of label (2–7%) was associated with extracellular free choline at the start of the experiment. During the first three hours after the shift to unlabelled medium, the free choline from the medium was taken up, the water soluble intracellular pool declined to a few percent, and the label appeared in the lipid associated pool, which was shown to be greater than 90% PC. Very little label (10% or less of the total label) appeared in the medium throughout the six hour chase (FIG. 4A; FIG. 5). In the case of wild type cells, the extracellular label that did appear was not in the form of free choline (FIG. 5). Most likely, it is glycerophosphocholine, known to be excreted by wild type yeast cells as reported by Angus, W. W., et al., Arch. Biochem. Bio hys. 151:483 (1972), the disclosure of which is incorporated herein by reference.

In strains exhibiting the "cki1" pattern of choline metabolism (i.e., SEC14 cki1 at both 25° C. and 37° C., and sec14$^{ts}$ cki1 only at the permissive temperature of 25° C.), a greater proportion of total cellular label was present in the lipid fraction at the start of the. experiment (FIG. 4B). The water soluble intracellular pool was 12% or less of total label. In the SEC14 cki1 strain at both temperatures, as well as the sec14$^{ts}$ cki1 strain at 25° C., there was little or no transfer of label from the intracellular soluble pool to PC following the shift to unlabelled medium. However, steady loss of label from PC (about 7% in three hours) was observed, with a corresponding appearance of label associated with free choline in the growth medium (shown for the SEC14 cki1 strain at 37° C. in FIG. 4B and FIG. 5).

Finally, a third and very distinctive pattern of PC turnover was exhibited by the sec14$^{ts}$ cki1 strain at 37° C. (FIG. 4C). At 37° C., the sec14$^{ts}$ cki1 strain had an initial label distribution at the time of shift to unlabelled medium similar to the SEC14 cki1 strain, but it lost label from PC much more rapidly (54% in the first three hours). Again, the label appeared in the medium as free choline (FIG. 4C; FIG. 5). This finding is consistent with the strong Opc$^-$ phenotype associated with the sec14$^{ts}$ cki1 strain at 37° C. (FIG. 3). The exception of the sec14$^{ts}$ cki1 strain at 37° C., the PI content of all of the strains grown at 25° C. or 37° C. in I$^-$ medium was between 9–15% of the total phospholipid. In I$^+$ medium at 37° C. in all of the strains tested, the proportion of PI was 28–32% of total phospholipid (Table III).

TABLE III

Effect of inositol and temperature on phospholipid composition
Yeast strains were grown for five to six generations at the indicated temperatures in I$^+$ or I$^-$ medium containing 10 μCi/ml [$^{32}$P]orthophosphate. The cells were harvested, and phospholipids extracted and resolved as described under "Example." The term "Other" includes CDP-DG, PMME, PDME, CL and polar lipids, including sphingolipids, remaining near the origin. Values represent the percentage of total lipid associated $^{32}$P incorporated into each phospholipid species.

| Strain | Med. | Temp.(°C.) | Phospholipid Composition (% total) | | | | | |
|---|---|---|---|---|---|---|---|---|
| | | | PI | PC | PE | PS | PA | Other |
| | I$^-$ | 25 | | | | | | |
| wt(SEC14 CKI1) | | | 9.0 | 49.4 | 14.2 | 7.8 | 1.6 | 18.0 |
| sec14$^{ts}$ CKT1 | | | 11.9 | 48.2 | 13.3 | 5.6 | 1.3 | 19.8 |
| SEC14 cki1 | | | 12.7 | 47.4 | 15.9 | 5.0 | 0.9 | 18.1 |
| sec14$^{ts}$ cki1 | | | 12.9 | 44.5 | 15.9 | 5.9 | 1.5 | 19.3 |
| | I$^-$ | 30 | | | | | | |
| wt | | | 10.8 | 46.8 | 13.4 | 8.4 | 1.6 | 19.0 |
| sec14$^{ts}$ cki1 | | | 14.1 | 45.6 | 13.6 | 7.6 | 1.1 | 18.0 |
| | I$^-$ | 37 | | | | | | |
| wt | | | 8.8 | 48.1 | 11.1 | 8.6 | 1.6 | 21.8 |
| SEC14 ccki1 | | | 14.9 | 39.5 | 14.3 | 6.9 | 1.2 | 23.2 |
| sec14$^{ts}$ cki1 | | | 19.4 | 30.9 | 19.5 | 6.6 | 1.6 | 22.0 |
| | I$^+$ | 37 | | | | | | |
| wt | | | 28.2 | 35.9 | 9.5 | 7.0 | 1.1 | 18.3 |
| SEC14 ccki1 | | | 31.6 | 35.7 | 7.7 | 6.0 | 1.4 | 17.6 |
| sec14$^{ts}$ cki1 | | | 29.5 | 23.3 | 19.4 | 5.7 | 1.5 | 20.6 | loss of $^{14}$C label from PC in the sec14$^{ts}$ cki1 and SEC14 cki1 strains was also examined when the cells were labelled with $^{14}$C choline to steady-state at 25° C. and were shifted to unlabelled medium at 37° C. The SEC14 cki1 strain, which had identical patterns of turnover at 25° C. and 37° C. (FIG. 4B), not surprisingly showed a similar labelling pattern when shifted from 25° C. to 37° C. However, when shifted to 37° C. after labelling at 25° C., the sec14$^{ts}$ cki1 strain, which had different labelling patterns at the two temperatures, exhibited the pattern of $^{14}$C loss from PC observed when the labelling and the turnover were both carried out at 37° C. (FIG. 4C). Thus, it is concluded that the accelerated pattern of turnover must have occurred immediately upon shifting the sec14$^{ts}$ cki1 strain to 37° C.

Figure 6D:
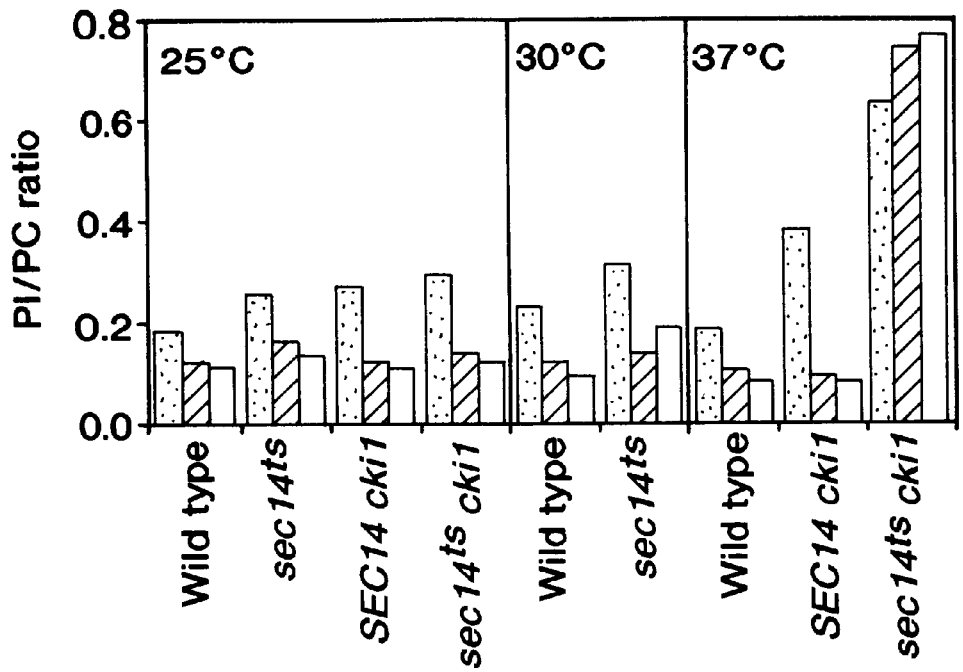
Figure 6E:
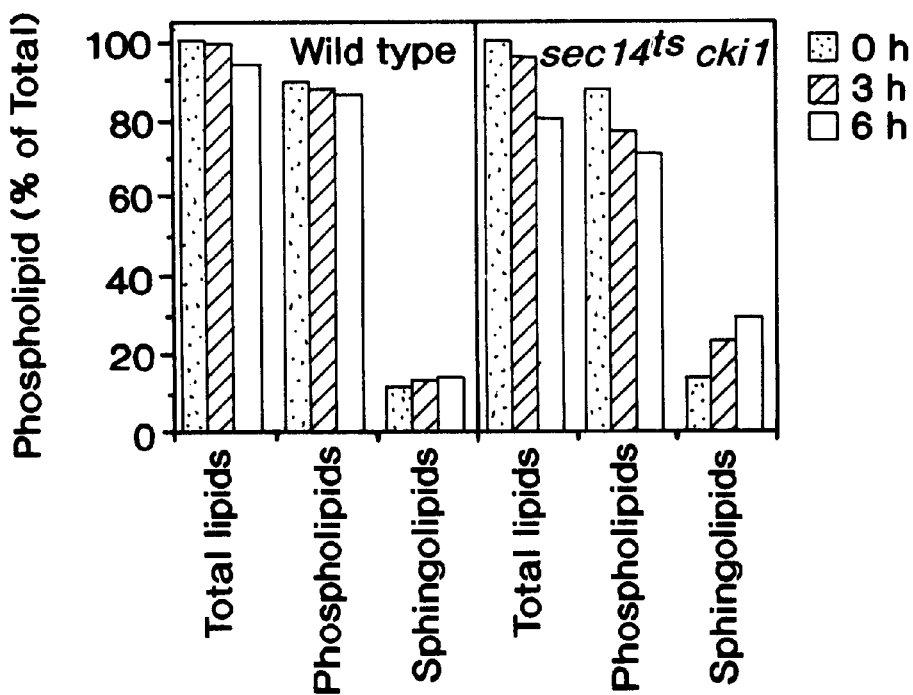

Phospholipid composition. At 25° C. in I$^-$ medium, all four strains exhibited phospholipid compositions (Table III below) similar to each other and to other published reports for these as described by McGee, T. P., et al. (1994), and other strains, as described by Paltauf, F., et al. (1992), under similar growth conditions. The compositions of the sec14$^{ts}$ cki1 and wild type strains grown in I$^-$ medium were also analyzed at 30° C. and were found to be similar to the compositions obtained at 25° C. In I$^+$ medium at 37° C., the three strains capable of growth (i.e., wild type, SEC14 cki1 and sec14$^{ts}$ cki1) exhibited phospholipid compositions similar to those previously reported for this growth condition by McGee, T. P., et al. (1994). In general, the phospholipid compositions of cells grown in I$^+$, compared to I$^-$ medium, contained a higher proportion of PI (Table III). At 37° C. in I$^-$ medium, the sec14$^{ts}$ cki1 strain, however, contained a proportion of PI (19% of total cellular phospholipids) approximately twice the proportion of PI observed in the wild type strain under these same growth conditions. With Phospholipid turnover. Cells were labelled to steady-state with $^{32}$P, as shown in Table III, and the retention and distribution of the $^{32}$P into the various phospholipids was tracked after shifting the cells into unlabelled medium (FIG. 6). At 25° C., no distinctive differences among the four strains were observed (data not shown). At 37° C., the patterns of $^{32}$P label retention in the wild type and SEC14 cki1 strains (FIGS. 6A and 6B) were similar to each other and to the results obtained in all four strains at 25° C. (data not shown). In all four strains at 25° C., and in wild type and SEC14 cki1 cells at 37° C. (FIGS. 6A and 6B), label was gradually lost from all lipids, except PC, where it accumulated. In all cases except sec14$^{ts}$ cki1 at 37° C. (FIG. 6C), the ratio of label remaining in PI vs. PC tended to decrease over time (FIG. 6D). In sec14$^{ts}$ cki1 at 37° C., however, the PI/PC ratio started high and increased during the course of the six hour turnover experiment. The label associated with the category "other," which includes sphingolipids, also rose in the sec14$^{ts}$ cki1 strain during the course of the turnover experiment at 37° C. In the sec14$^{ts}$ cki1 strain at 37° C., sphingolipids accumulated label during the course of the experiment (FIG. 6E). In the sec14$^{ts}$ cki1 strain, the proportion of label associated with PA remained fairly constant over time (FIG. 6C), whereas it dropped about two-fold in the wild type (FIG. 6A) and in the SEC14 cki1 (FIG. 6B) strains in the first three hours after transfer to unlabelled medium.

Pulse labelling of phospholipids. Because of the nature of the product-precursor relationship shown in FIG. 1, $^{32}$P introduced during a 30 minute pulse labelling period will show a very different pattern of distribution than during steady-state labelling used to assess phospholipid composition (Table III). The three strains able to grow at 37° C. were pulse labelled with $^{32}$P for 30 minutes and in all three cases, the overall incorporation was greater per OD unit of culture in I⁺ medium compared to I⁻ medium (Table IV below). The ratio of label recovered in association with PI compared to PC (PI/PC ratio) was higher in all three strains grown in I⁺ as opposed to I⁻ medium (Table IV). However, in I⁻ medium in the sec14$^{ts}$ cki1 strain, a higher proportion of label was associated with PI and there was a higher PI/PC ratio than in either the wild type strain or the SEC14 cki1 strain.

Figure 7:
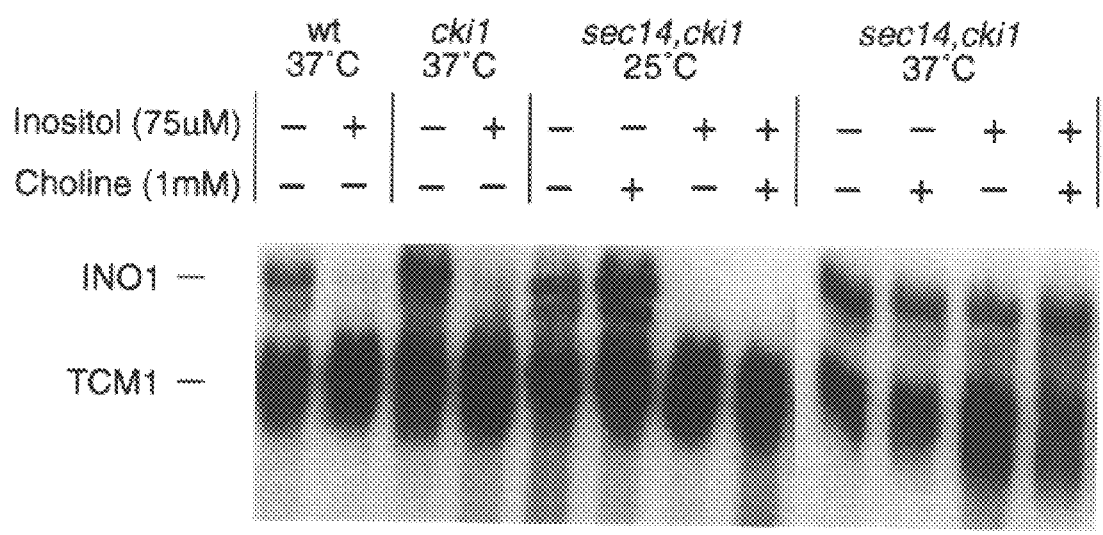
FIG. 7 shows Northern blot analysis of INO1 expression in wild type (wt), SEC14 cki1 (cki1), and sec14$^{ts}$cki1 (sec14, cki1) strains at 25° and 37°. Strains were grown in I$^+$ or I$^-$ media or C$^+$ or C$^-$ media, as indicated. RNA was extracted and Northern blot analysis was performed as described herein. Hybridization with the TCM1 probe served as a loading control.

When examined at 25° C., the sec14$^{ts}$ CKI1 strain showed a pattern of label incorporation during the 30 minute pulse that was similar to the wild type strain at 37° C. The sec14$^{ts}$ CKI1 and sec14$^{ts}$ cki1 strains were also pulse labelled with $^{32}$P following a shift from 25° C. to 37° C. in I⁺ or I⁻ media. The labelling pattern of the sec14$^{ts}$ cki1 strain under these conditions (Table IV, part B) was quite similar to the pattern seen when the same strain was maintained continuously at 37° C. in I⁺ or I⁻ media. However, the sec14$^{ts}$ CKI1 strain incorporated less $^{32}$P label per OD unit of culture four hours after the shift to 37° C. as compared to the sec14$^{ts}$ cki1 strain and a much higher proportion of the label was incorporated into PC in the CKI1 strain at 37° C. than in any other strain tested under any growth condition (Table IV, part B).

was investigated in the four strains: wild type (SEC14 CKI1), sec14$^{ts}$ CKI1, SEC14 cki1 and sec14$^{ts}$ cki1. At 25° C., all four strains showed repression of the INO1 transcript in response to inositol when tested by Northern blot analysis (FIG. 7; Table V below). The sec14$^{ts}$ CKI1 strain was also examined at 30° C. and showed normal regulation. At 25° C. or 30° C. in each of these strains, the INO1 transcript is substantially repressed (i.e., ten-fold or more) in cells grown in I⁺ medium compared to cells grown in F medium (FIG. 7; Table V).

At 37° C., only three of the strains will grow: wild type, SEC14 cki1, and sec14$^{ts}$ cki1. The wild type and SEC14 cki1 strains both exhibited normal regulation of INO1 at 37° C. (Table V, FIG. 7). However, consistent with its is Opi⁻ phenotype, the sec14$^{ts}$ cki1 strain showed an abnormal pattern of INO1 expression at 37° C. In the absence of inositol, the INO1 transcript was expressed at a level somewhat higher than the wild type derepressed level. Furthermore, when inositol was added to the growth medium, in the absence of choline, the level of INO1 transcript was repressed only about two-fold, compared to

TABLE IV

Pulse labeling of Phospholipids
In A, strains grown to mid-log phase (OD$_{595}$ = 0.4–0.6) in I⁺ or I⁻ medium at the indicated temperatures were pulsed for 30 minutes with 50 μCi/ml [$^{32}$P]orthophosphate. The lipids were then extracted and analyzed as described in "Example." In B, yeast cells were grown at 25° C. and then shifted to 37° C. After four hours of growth, the cells were pulse-labeled for 30 minutes with 50 μCi/ml [$^{32}$P]orthophosphate. The lipids were extracted and analyzed. The amount of $^{32}$P incorporated into lipid ($^{32}$P Incorp.) is presented as CPM per optical density unit at A$_{595}$ × 10$^3$ (CPM/ODUX10$^3$). The relative percentage of [$^{32}$P] label in the individual phospholipid species is presented as a percentage of the total $^{32}$P incorporated into lipid. The PI/PC ratio was calculated from the percentages of PI versus PC. "Other" lipids include CDP-DG, PMME, PDME, cardiolipin (CL), as well as polar lipids that remained near the origin.

A. Pulse labeling at indicated temperatures.

| | | | | $^{32}$P in phospholipid (% of total) | | | | | | |
|---|---|---|---|---|---|---|---|---|---|---|
| Strain | Temp. (°C.) | Med. | $^{32}$P Incorp. (CPM/ODUX10$^3$) | PI | PC | PS | PE | PA | Other | PI/PC |
| wt (SEC14 CKI1) | 37 | I⁺ | 213.4 | 42.3 | 6.7 | 22.4 | 11.4 | 2.5 | 14.7 | 6.31 |
| SEC14 cki1 | 37 | I⁺ | 175.4 | 45.2 | 5.8 | 21.3 | 11.8 | 2.7 | 13.2 | 7.79 |
| sec14$^{ts}$ cki1 | 37 | I⁺ | 167.8 | 39.9 | 6.4 | 15.3 | 26.9 | 2.0 | 9.5 | 6.23 |
| wt | 37 | I⁻ | 95.8 | 20.2 | 10.5 | 22.8 | 10.8 | 6.4 | 29.2 | 1.92 |
| SEC14 cki1 | 37 | I⁻ | 101.4 | 24.1 | 6.6 | 24.3 | 11.6 | 6.0 | 27.5 | 3.65 |
| sec14$^{ts}$ cki1 | 37 | I⁻ | 93.8 | 30.0 | 6.4 | 20.4 | 27.8 | 3.0 | 12.4 | 4.69 |
| sec14$^{ts}$ CKI1 | 25 | I⁺ | 163.2 | 37.5 | 6.2 | 24.6 | 17.1 | 2.3 | 12.2 | 6.05 |
| sec14$^{ts}$ CKI1 | 25 | I⁻ | 130.6 | 17.3 | 15.0 | 25.1 | 12.6 | 6.5 | 23.6 | 1.15 |

B. Pulse labeling after temperatures shift from 25° C. to 37° C.

| | | $^{32}$P in phosphohpid (% of total) | | | | | | |
|---|---|---|---|---|---|---|---|---|
| Strain | Med. | $^{32}$P Incorp. (CPM/ODUX10$^3$) | PI | PC | PS | PE | PA | Other | PI/PC |
| sec14$^{ts}$ CKI1 | I⁺ | 36.6 | 41.7 | 23.8 | 12.0 | 8.4 | 2.7 | 11.4 | 1.75 |
| sec14$^{ts}$ CKI1 | I⁻ | 16.4 | 21.8 | 27.9 | 16.3 | 6.9 | 5.1 | 22.0 | 0.78 |
| sec14$^{ts}$ cki1 | I⁺ | 277.2 | 41.1 | 7.9 | 14.9 | 24.9 | 2.8 | 8.7 | 5.20 |
| sec14$^{ts}$ cki1 | I⁻ | 74.0 | 30.3 | 8.4 | 19.3 | 19.4 | 4.6 | 18.0 | 3.61 |

Regulation of the INO1 in the sec14$^{ts}$ cki1 strain. The Opi⁻ phenotype, observed in the sec14$^{ts}$ strain at 37° C., is associated with misregulation of INO1, as reported by Greenberg, M., et al. (1982). Therefore, INO1 regulation more than ten-fold repression seen in the wild type strains (Table V). When inositol and choline were added together to the growth medium, no repression of INO1, at all, was seen in the sec14$^{ts}$ cki1 strain at 37° C. (Table V).

TABLE V

Effect of inositol and choline on INO1 gene expression as measured by Northern blot quantitation
Quantitation of Northern blot analysis shown in FIG. 4. Strains were grown in $I^+$ or $I^-$ medium with ($C^+$) or without ($C^-$) 1 mM choline. RNA analysis was performed as described in "Example". Hybridization with the TCM1 probe served as a loading control. Quantitation was performed with an AMBIS 4000 phosphoimager. Data is expressed as a percentage of the expression observed in the wild type (wt) strain at 37° C. in $I^-C^-$ conditions.

| | | INO1 Expression (%) | | | |
|---|---|---|---|---|---|
| Strain | Temp. | $I^-C^-$ | $I^-C^+$ | $I^+C^-$ | $I^+C^+$ |
| wt(SEC14 CKI1) | 25° C. | 116 | np[a] | 6 | np |
| sec14$^{ts}$ CKI1 | " | 83 | 57 | 6 | 6 |
| SEC14 cki1 | " | 153 | np | np | 16 |
| sec14$^{ts}$ cki1 | " | 103 | 119 | 6 | 9 |
| sec14$^{ts}$ CKI1 | 30° C. | 150 | 116 | 9 | 3 |
| wt | 37° C. | 100 | np | np | 13 |
| SEC14 cki1 | " | 128 | np | np | 19 |
| sec14$^{ts}$ cki1 | " | 163 | 163 | 72 | 209 |

[a]np, not performed

Kinetics of INO1 induction in the sec14$^{ts}$ cki1 strain shifted to 37° C. In order to study the kinetics of INO1 induction, the INO1 lacZ reporter construct was used as described in the Example. This construct was transformed into the four strains used to study INO1 regulation and the strains were assayed for β-galactosidase activity under various growth conditions. In order to establish that the reporter construct was regulated in a fashion resembling the native INO1 transcript (FIG. 7; Table V), expression of β-galactosidase in cells grown to mid-logarithmic phase was initially studied (Table VI below). The sec14$^{ts}$ CKI1 strain will not grow at 37° C. and, therefore, only three of the four strains, namely wild type, SEC14 cki1 and sec14$^{ts}$ cki1, were tested at 37° C. The overall pattern of expression of the INO1 lacZ construct (Table VI) was very similar to the expression of the native INO1 transcript measured by Northern blot analysis (Table 5, FIG. 7). At 25° C. and 30° C., all four strains showed β-galactosidase regulation in response to inositol comparable to wild type, except that the sec14$^{ts}$ cki1 strain had a slightly higher level of β-galactosidase under repressing conditions ($I^+$ medium). At 37° C., the wild type and SEC14 cki1 strains, showed the normal pattern of regulation; i.e., repression of INO1 lacZ in response to inositol, while the sec14$^{ts}$ cki1 strain exhibited misregulation of INO1 lacZ at 37° C. (Table VI). Consistent with its Opi$^-$ phenotype and results obtained by Northern blot analysis of INO1 transcript (Table V, FIG. 7) at 37° C. in $I^-$ medium, the sec14$^{ts}$ cki1 strain expressed a level of β-galactosidase about two-fold higher than its wild type and SEC14 cki1 counterparts. Also consistent with Northern blot analysis (Table V) in $I^+$ medium at 37° C., only about a two-fold repression of the INO1 lacZ reporter construct was observed in the sec14$^{ts}$ cki1 strain (Table VI).

Figure 8A:
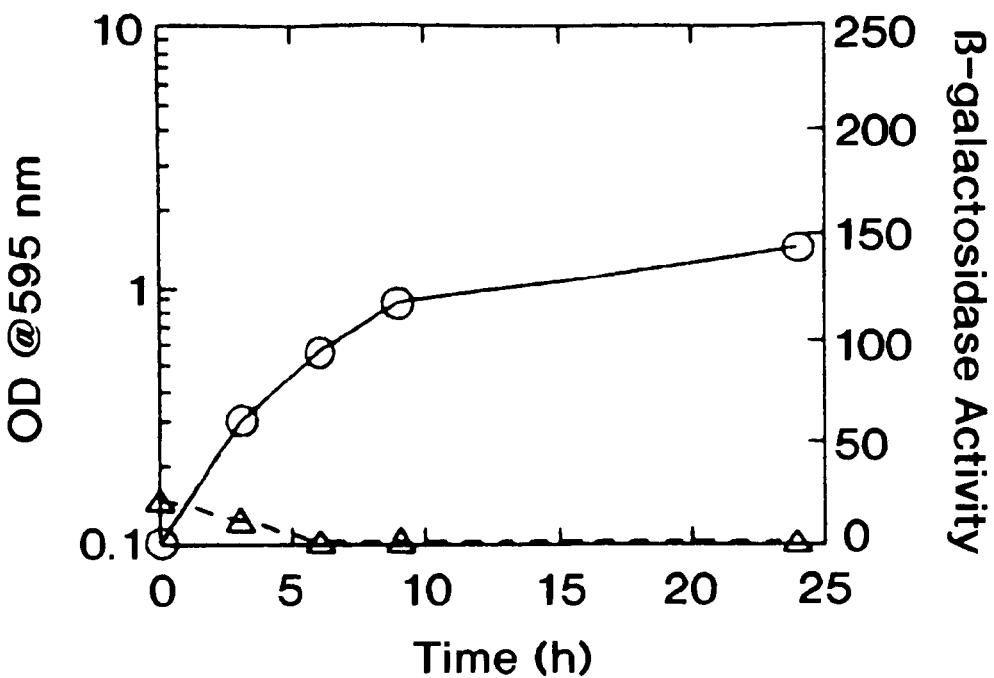
FIGS. 8A–8H show kinetics of INO1 derepression in sec14 and sec14$^{ts}$cki1 mutants. Yeast strains containing plasmid pJH359 were grown at 25° C. under repressing conditions (I⁺ medium), to the mid-logarithmic phase of growth. The cells were harvested by filtration and transferred to fresh media (I⁺ or I⁻) at the permissive (25° C.) or non-permissive (37° C.) temperature. At the indicated time points, the $OD_{595}$ of the cultures (○) and β-galactosidase activity (Δ) was determined.
Figure 8B:
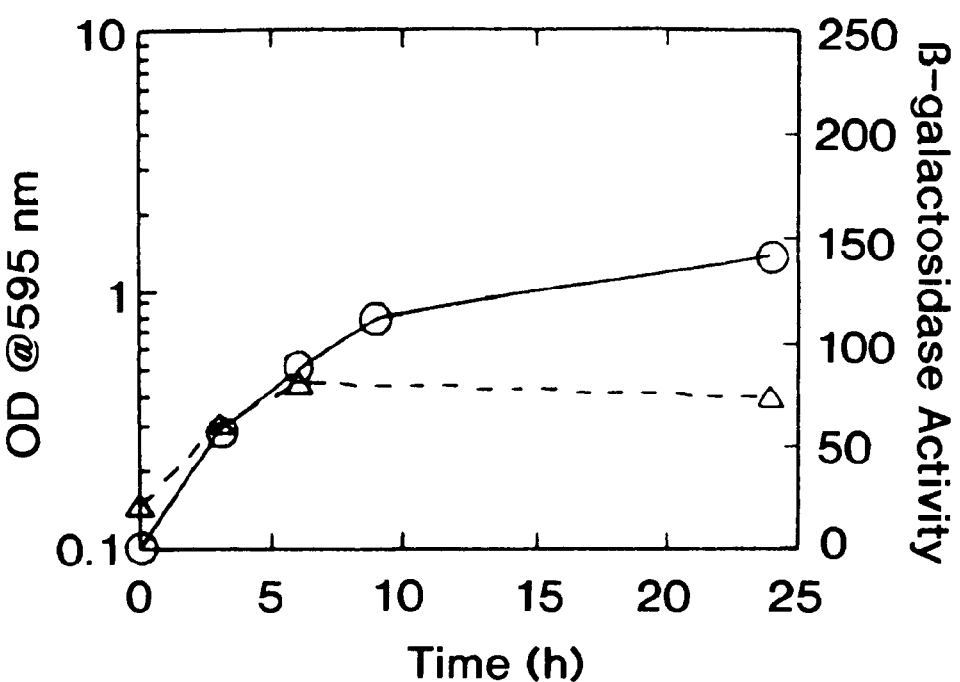
Figure 8C:
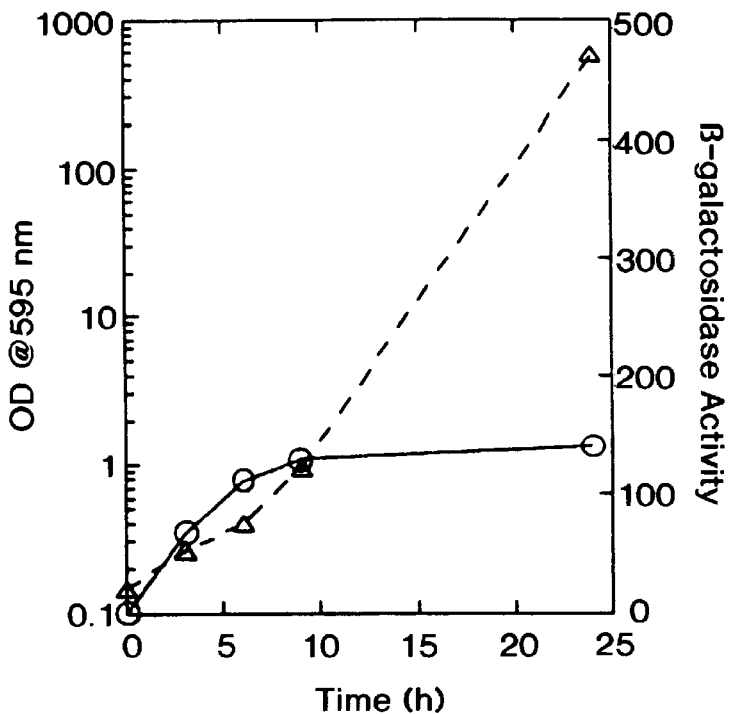

Using the reporter construct containing the lacZ gene under the control of an INO1 promoter fragment, the kinetics of INO1 derepression was investigated. At 25° C., all three strains tested (wild type, sec14$^{ts}$ CKI1, sec14$^{ts}$ cki1) showed rapid derepression of the INO1 lacZ construct when shifted from $I^+$ medium to $I^-$ medium (data shown only for sec14$^{ts}$ cki1; FIG. 8B). The wild type strain showed a similar pattern of derepression when shifted from $I^+$ medium at 25° C. to $I^-$ at 37° C. (FIG. 8H). In each of these cases, β-galactosidase activity plateaued as the cultures approached stationary phase, indicating that new expression of β-galactosidase had stopped, as expected, at about the time when INO1 expression is known to be repressed as cells enter stationary phase as described by Lamping, E., et al., *Genetics* 137:55 (1995); Griac, P., et al., *NATO ASI Series: Molecular Dynamics of Biological Membranes* (Op den Kamp, J. A. F., ed.) Vol. H96, pp. 339–346, Spinger-Verlag, Berlin/Heidelberg (1996); and Jiranek, V., et al., *J. Bacterial.* (submitted) (1997), the disclosures of which are incorporated herein by reference.

Figure 8D:
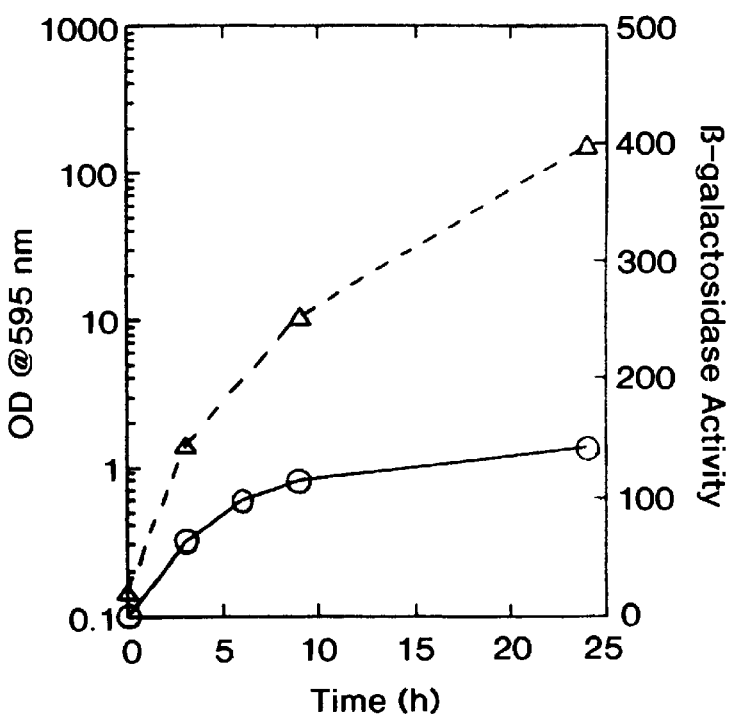
Figure 8E:
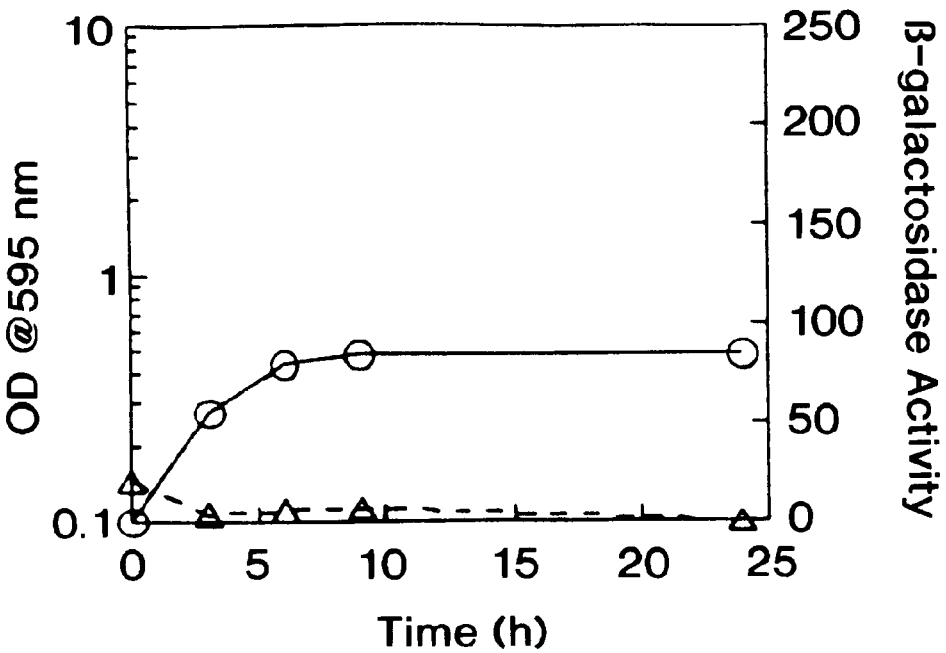
Figure 8F:
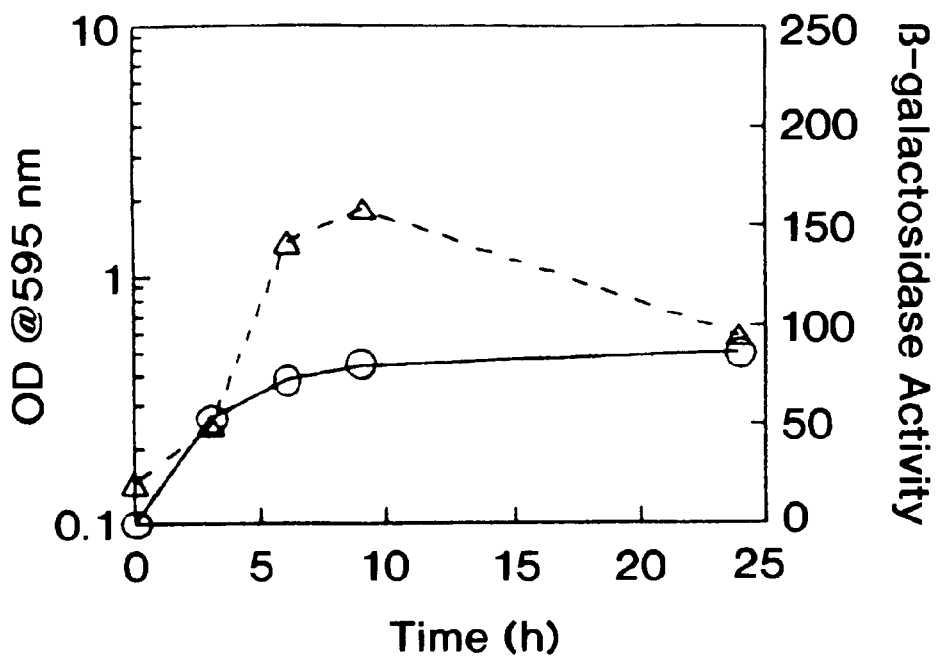
Figure 8G:
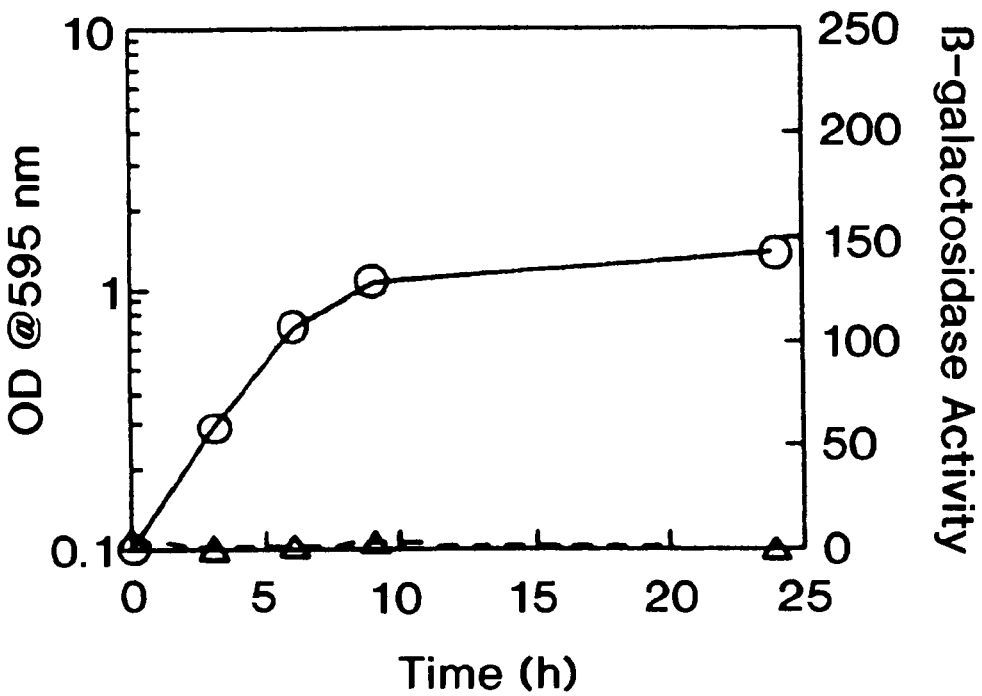
Figure 8H:
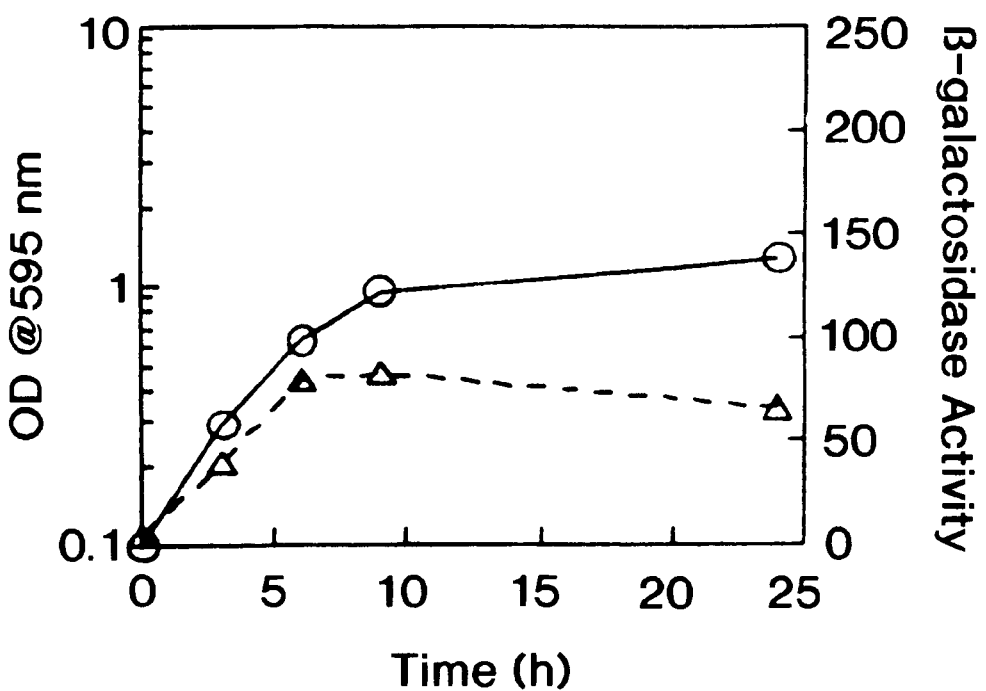

Upon shift from $I^+$ medium at 25° C. to $I^-$ medium at 37° C., the INO1 lacZ construct in the sec14$^{ts}$ cki1 strain showed more rapid derepression than in other strains shifted to $I^-$ medium (FIG. 8D). Unlike wild type shifted to $I^-$ at 37° C. (or any of the three strains shifted from $I^+$ to $I^-$ at 25° C.), derepression of the INO1 lacZ construct in the sec14$^{ts}$ cki1 strain at 37° C. continued well into stationary phase. The sec14$^{ts}$ cki1 strain shifted from $I^+$ medium at 25° C. to $I^+$ at 37° C. also exhibited derepression of β-galactosidase. The initial derepression of the INO1 lacZ construct in the sec14$^{ts}$ cki1 strain shifted from 25° C. to 37° C. in $I^+$ medium was less rapid than when the cells were shifted to $I^-$ medium at 37° C. However, at 37° C., even in $I^+$ medium, the derepression of the INO1 construct continued after the sec14$^{ts}$ cki1 cells became stationary. The sec14$^{ts}$ CKI1 strain stopped growing after five to six hours upon shifting to 37° C. (FIGS. 8E and 8F). However, under these conditions the INO1 lacZ construct derepressed in $I^+$ medium to a level exceeding the wild type strain grown under comparable conditions (compare FIGS. 8F [sec14$^{ts}$ CKI1] and FIG. 8H [wild type]. When shifted from 25° C. to 37° C. in $I^+$ medium, no derepression of the INO1 lacZ construct was observed in the sec14$^{ts}$ CKI1 strain (FIG. 8E).

TABLE VI

Effect of inositol and temperature on INO1 gene expression as measured by β-glactosidase activity
Various yeast strains were transformed with plasmid pJH359 as described in "Example." The strains were grown in $I^+$ or $I^-$ medium at the indicated temperature to the mid-logarithmic phase of growth and assayed for β-galactosidase activity. Data presented here represents an average ± standard deviation of three experiments using independent transformants.

| | β-Galactosidase Activity | | | | | |
|---|---|---|---|---|---|---|
| | 25° C. | | 30° C. | | 37° C. | |
| Strain | $I^+$ | $I^-$ | $I^+$ | $I^-$ | $I^+$ | $I^-$ |
| wild type | 3 ± 3 | 86 ± 21 | 2 ± 1 | 125 ± 21 | 10 ± 9 | 124 ± 10 |
| cki1 | 3 ± 3 | 88 ± 14 | np[b] | np | 5 ± 5 | 199 ± 30 |
| sec14 | 9 ± 3 | 142 ± 49 | 11 ± 7 | 174 ± 33 | np | np |
| sec14, cki1 | 22 ± 8 | 154 ± 56 | np | np | 155 ± 57 | 333 ± 74 |

[a]β-galactosidase activity = 1000 × ($OD_{420}$/min/mg protein)
[b]np, not performed.

IV. DISCUSSION

Studies using wild type yeast cells have detected very little PC turnover as described by Angus, W. W., et al. (1972). Consistent with these earlier studies, the analysis herein of PC turnover in wild type yeast using both $^{32}P$ and $^{14}C$ choline label, revealed very little evidence of extensive PC turnover (FIGS. 4, 5 and 6). In cells carrying a mutation in the CDP-choline pathway, it is possible to examine phospholipid metabolism under conditions in which reutilization of the choline liberated by PC turnover is largely blocked. Under these circumstances substantial PC turnover was detected and the choline liberated by this process appeared in the growth medium (FIGS. 4 and 5) providing a phenotype (Opc$^-$) that is readily detected in a plate assay (FIG. 3). It is believed that the extent of PC turnover is similar in wild type, but that choline liberated by turnover in wild type cells is immediately re-incorporated into PC via the CDP-choline pathway. Thus, the cki1 (cct1 or cpt1) genetic backgrounds provide unique opportunities to explore the extent of PC turnover in yeast.

The choline excretion phenotype provides, for the first time in yeast, a means of estimating the extent of activity in the CDP-choline pathway in cells growing in the absence of choline. Recent studies have suggested that this pathway contributes substantially to PC biosynthesis even in the absence of exogenous choline as described by McMaster, C. R., et al. (1994); McDonough, V. M., et al. (1995); and McGee, T. P., et al. (1994). The present invention substantiates this hypothesis. Reutilization of choline liberated by turnover appears to be a major function of the CDP-choline pathway in yeast cells growing in the absence of choline. Based on the choline excreted by the SEC14 cki1 strain at 37° C. (FIGS. 4 and 5), it is estimated that some 7% of cellular choline is recycled via PC turnover and re-synthesis in each generation period (about three hours). This is believed to be an underestimate, however, because cki1 cells retain some capacity to reuse free choline, as evidenced by the ability to label the cells with $^{14}C$ choline in the first place. Nevertheless, it is possible to use the choline excretion plate assay plate phenotype (Opc$^-$) to carry out a qualitative comparison of the extent of PC turnover in different strains, under different growth conditions. For example, in the SEC14 cki1 strain, it was observed that the extent of the choline excretion ring was affected by temperature and by the presence of inositol (FIG. 3, Table 2).

The nature of PC turnover in yeast. It is believed that the free choline found in the growth medium of the cki1-bearing strains most likely arises from phospholipase D (PLD)-mediated PC turnover which produces free choline and phosphatidic acid (PA). It is now recognized that PLD-mediated hydrolysis is a major route of PC breakdown in a variety of mammalian cell types as described by Exton, J. H., *Biochim. Biophys. Acta* 1212:26 (1994). The bulk of the $^{14}C$ choline excreted by the SEC14 cki1 strain detected in the growth medium was free choline (FIG. 5). This is not consistent with phospholipase B (PLB)-mediated turnover, which produces glycerophosphocholine as reported by Lee, K. S., et al., *J. Biol. Chem.* 269:19725 (1994), rather than free choline. Neither can phospholipase C (PLC)-mediated turnover, which produces choline phosphate and diacylglycerol (DAG), readily account for the free choline excreted by the cki1 mutant. Moreover, it is believed that PC turnover accelerates via a PLD mechanism when the sec14$^{ts}$ cki1 mutant is raised to the restrictive temperature, resulting in increased choline excretion. Consistent with this hypothesis, it was found that the $^{14}C$ label that appears in the medium of the sec14$^{ts}$ cki1 strain at 37° C. is again predominantly free choline and that the generation of this pool of choline correlates with the loss of label from PC (FIGS. 4 and 5). At 37° C., the sec14$^{ts}$ cki1 strain lost more than 50% of its PC associated $^{14}C$ choline label in three hours (FIGS. 4 and 5), or approximately one generation time. The cki1 strain, in contrast, lost approximately 7% of its PC associated label in this same amount of time.

When PC turnover occurs via a PLD-mediated route, one molecule of PA is generated for every molecule of free choline produced and the associated $^{32}P$ label is not lost from the lipid fraction (FIG. 1). Lipid associated-$^{32}P$ label recycled via PLD reenters into the PA pool and can be directly reused in the series of reactions leading to the reformation of PC via the PE methylation pathway using CDP-DG, PS, and PE as intermediates. Recycled, labelled PA can also serve as a precursor to PI, via the CDP-DG branchpoint in the pathway, as shown in FIG. 1. In the studies shown in FIG. 6, the distribution of label from $^{32}P$ into the various lipids in wild type and SEC14 cki1 cells three and six hours after removal from labelled medium reveals that total $^{32}P$ is only slowly lost from the chloroform soluble pool. Even in sec14$^{ts}$ cki1 cells, which lose 50% or more of the $^{14}C$ choline label associated with PC per generation at 37° C., $^{32}P$ is lost very slowly from the total lipid pool. These results are consistent with major turnover occurring via a PLD mediated mechanism, as discussed above. These observations also explain why substantial PC turnover has not been detected previously in labelling studies of wild type yeast cells as described by Angus, W. W., et al. (1972). In contrast to PLD-mediated turnover, the PLC and PLB-mediated routes of phospholipid turnover are predicted to lead to loss of $^{32}P$ from the chloroform soluble pool because the $^{32}P$ label is cycled into water soluble products such as choline phosphate and glycerophosphocholine (FIG. 1). The present data, therefore, suggests that the majority of PC turnover in yeast cells is carried out via a PLD-mediated mechanism.

While $^{32}P$ was lost only slowly from total lipid in the sec14$^{ts}$ cki1 mutant at 37° C., the pattern of $^{32}P$ distribution during the six hour chase was strikingly different than that observed in the same strain at 25° C. or in any of the other strains, including SEC14 cki1 at 37° C. In the sec14$^{ts}$ cki1 strain at 37° C., the ratio of PI to PC was high at the start of the turnover experiment and, unlike the other strains, this ratio increased as the experiment progressed. At 37° C. in the sec14$^{ts}$ cki1 strain, $^{32}P$ label tended to accumulate in PI and in the category "other," which includes sphingolipids (FIG. 6), a pattern consistent with elevated turnover via a PLD mediated mechanism. Each time PC serves as a substrate in PLD mediated turnover, PC associated $^{32}P$ recycles as PA and has a certain probability of passing into PI and then into sphingolipids. Accumulation of lipid associated $^{32}P$ into PI and inositol containing sphingolipids is, thus, an expected consequence of elevated PLD mediated turnover of PC. This pattern of label accumulation will be further accentuated when high amounts of inositol are present, either from exogenous sources or from endogenous synthesis, due to derepression of the INO1 gene, as discussed below.

Role of PC turnover in suppression of the sec14$^{ts}$ phenotype. It is not believed that accelerated turnover of PC is the cause of lethality in the sec14$^{ts}$ CKI1 strain when this strain is elevated to the restrictive temperature. The sec14$^{ts}$ cki1 strain grows quite well at 37° C. in the absence of a functional SEC14 gene product and yet exhibits greatly increased PC turnover (FIGS. 4 and 5). Indeed, in the face of massive ongoing PC turnover, this strain has a doubling time comparable to that of the wild type and SEC14 cki1 strains. It is proposed that the cki1 lesion suppresses the lethality caused by inactivation of Sec14p at the restrictive temperature precisely because it prevents the resynthesis of PC following accelerated turnover. Sec14p appears to be required for removal of PC synthesized via the CDP-choline pathway from its immediate site of synthesis, presumably in the Golgi as described by McGee, T. P., et al. (1994). If PC is not removed by the action of Sec14p, its rate of turnover via PLD apparently increases, as seen in FIG. 4. Under such circumstances, in the sec14$^{ts}$ CKI1 strain when the CDP-choline pathway is not blocked, PC could be immediately resynthesized, setting up a futile cycle.

Role of PC turnover in regulation of the INO1 gene. It is believed that the derepression of the INO1 gene, which occurs rapidly following the shift of the sec14$^{ts}$ cki1 strain to 37° C. (FIGS. 8C and 8D) even in the presence of inositol, is directly correlated to and caused by the increase in the rate of PC turnover that occurs when Sec14p is inactivated. It has been known, as reported by Paltauf, F., et al. (1992) and Henry, S. A., *Molecular Biology of the Yeast Saccharomyces: Metabolism and Gene Expression* (Strathern, J. N., et al. eds.) Vol. 2, pp. 101–158, 2 vols., Cold Spring Harbor Laboratory, Cold Spring Harbor, N.Y. (1982), the disclosure of which is incorporated herein by reference, that there is an association between PC and inositol metabolism.

In the current study, it is demonstrated that elevation of the sec14$^{ts}$ cki1 strain to the restrictive temperature results in increased turnover of PC and also generates a signal for derepression of INO1. The derepression of INO1 that is observed upon shift to the restrictive temperature exhibits remarkably rapid kinetics (FIG. 8) and correlates to the increase in PC turnover. In a previous study by Griac, P., et al. (1996), strains were employed containing combinations of mutations in the PE methylation and CDP-choline routes for PC biosynthesis. In that study, it was demonstrated that no single metabolite in either pathway for PC biosynthesis correlated to the production of the signal for repression/derepression of INO1. The metabolic conditions previously tested for their roles in INO1 repression/derepression included relative PC content and free choline availability. Neither of these factors was correlated to INO1 derepression. Rather, the metabolic signal controlling INO1 regulation appeared to be linked to the overall ability of increased PC biosynthesis to stimulate cell growth as reported by Griac, P., et al. (1996). The data presented herein suggests that INO1 derepression is correlated to PC turnover. It is also believed that INO1 derepression occurs in response to a metabolic signal generated in the course of the overall alteration in phospholipid metabolism produced by increased PC turnover.

Although the invention has been described in detail for the purposes of illustration, it is to be understood that such detail is solely for that purpose and that variations can be made thereon by those skilled in the art without departing from the spirit and scope of the invention except as it may be limited by the claims.

We claim:

1. A method for increased production of choline and inositol, choline and inositol metabolites, and choline- and inositol-containing phospholipids in yeast, comprising the step of:
   increasing phosphatidylcholine (PC) turnover in said yeast by culturing a strain of yeast that contains a mutation in its phosphatidylinositol/phosphatidylcholine transfer protein and a mutation that blocks PC biosynthesis under conditions which increase PC turnover in said yeast which thereby results in production of choline and inositol, choline and inositol metabolites, and choline- and inositol-containing phospholipids.

2. The method of claim 1, wherein said increasing step, further comprises:
   culturing a yeast strain carrying a mutation in the SEC14 gene of said yeast and a mutation in at least one gene of the Kennedy pathway of said yeast; and
   recovering said choline and inositol, choline and inositol metabolites, and choline- and inositol-containing phospholipids.

3. The method of claim 2, wherein said mutation in said SEC14 gene is sec14$^{ts}$.

4. The method of claim 2, wherein said mutation in at least one gene of the Kennedy pathway of said yeast is selected from the group consisting of CKI1, CCT1, and CPT1.

5. The method of claim 2, wherein said yeast is of the type *Saccharomyces cerevisiae*.

6. The method of claim 3, wherein said yeast strain is cultured at a nonpermissive temperature for said strain which inactivates the gene product of said SEC14 gene in said strain.

7. The method of claim 3, wherein said strain is sec14$^{ts}$ cki1.

8. The method of claim 3, wherein said strain is sec14$^{ts}$ cct1.

9. The method of claim 3, wherein said strain is sec14$^{ts}$ cpt1.

10. A method for simultaneous accelerated phosphatidylcholine (PC) turnover and derepression of the INO1 gene in yeast, comprising:
    culturing a yeast strain harboring a mutation in the SEC14 gene of said yeast and a mutation in a gene in the Kennedy pathway of said yeast under conditions whereby the gene product of said mutated SEC14 gene is inactivated thereby causing said PC turnover and derepression of the INO1 gene in said yeast.

11. The method of claim 10, wherein said mutation in said SEC14 gene is sec14$^{ts}$.

12. The method of claim 10, wherein said mutation in said gene in the Kennedy pathway is selected from the group consisting of CKI1, CCT1, and CPT1.

13. The method of claim 10, wherein said yeast is of the type *Saccharomyces cerevisiae*.

14. The method of claim 11, wherein said yeast strain is cultured at a nonpermissive temperature for said strain which inactivates the gene product of said SEC14 gene in said strain.

15. The method of claim 11, wherein said strain is sec14$^{ts}$ cki1.

16. The method of claim 11, wherein said strain is sec14$^{ts}$ cct1.

17. The method of claim 11, wherein said strain is sec14$^{ts}$ cpt1.

18. A method for producing free choline in yeast, comprising:
    culturing a yeast strain harboring a mutation in the SEC14 gene of said yeast and a mutation in the CKI1 gene of said yeast under conditions that inactivate the Sec14p gene product of said SEC14 gene thereby increasing phosphatidyl (PC) turnover and causing excretion of free choline.

19. The method of claim 18, wherein said yeast strain is sec14$^{ts}$ cki1.

20. The method of claim 18, wherein said yeast strain is of the type *Saccharomyces cerevistae*.

21. The method of claim 19, wherein said yeast strain is cultured at a nonpermissive temperature for said strain which inactivates the gene product of said SEC14 gene in said strain.

22. A method for producing free choline and choline phosphate (C-P) in yeast, comprising:
    culturing a yeast strain harboring a mutation in the SEC14 gene and a mutation in the CCT1 gene of said yeast under conditions that inactivate the Sec14p gene product of said SEC14 gene thereby increasing phosphatidyl (PC) turnover and thereby producing free choline and choline phosphate (C-P).

23. The method of claim 22, wherein said yeast strain is sec14$^{ts}$ cct1.

24. The method of claim 22, wherein said yeast is of the type *Saccharomyces cerevisiae*.

25. The method of claim 23, wherein said yeast strain is cultured at a nonpermissive temperature for said strain which inactivates the gene product of said SEC14 gene in said strain.

26. A method for producing free choline, choline phosphate (C-P), and cytidinediphosphate choline (CDP-C) in yeast, comprising:

culturing a yeast strain harboring a mutation in the SEC14 gene and a mutation in the CPT1 gene under conditions that inactivate the Sec14p gene product of said SEC14 gene thereby increasing phoshatidyl (PC) turnover and thereby producing free choline, choline phosphate (C-P), and cytidinediphosphate choline (CDP-C).

27. The method of claim 26, wherein said yeast strain is sec14$^{ts}$ cpt1.

28. The method of claim 26, wherein said yeast is of the type *Saccharomyces cerevisiae*.

29. The method of claim 27, wherein said yeast strain is cultured at a nonpermissive temperature for said strain which inactivates the gene product of said SEC14 gene in said strain.

30. A method for detecting phospholipase D-mediated turnover of phosphatidylcholine in vivo in yeast, comprising:

performing an assay for choline excretion which excretion is a result of phospholipase D-mediated turnover of phosphatidylcholine in said yeast.

31. The method of claim 30, wherein said assay is a plate assay utilizing a choline auxotrophic strain.

32. The method of claim 31, wherein said choline auxotrophic strain is cho2 opi3.

33. A plate assay for detecting choline excretion from phosphatidylcholine (PC) turnover in yeast growing on a plate, comprising:

detecting the choline excretion of said yeast strain by visualizing the growth of a choline auxotrophic strain placed onto said plate with said yeast.

34. The assay of claim 33, wherein said choline auxotrophic strain is cho2 opi3.

* * * * *